(12) United States Patent
Compaan et al.

(10) Patent No.: US 11,413,808 B2
(45) Date of Patent: Aug. 16, 2022

(54) CROSS-LINKABLE MICROGEL COMPOSITE MATRIX BATH FOR EMBEDDED BIOPRINTING OF PERFUSABLE TISSUE CONSTRUCTS

(71) Applicant: University of Florida Research Foundation, Incorporated, Gainesville, FL (US)

(72) Inventors: Ashley M. Compaan, Gainesville, FL (US); Yong Huang, Gainesville, FL (US); Kaidong Song, Gainesville, FL (US); Wenxuan Chai, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 243 days.

(21) Appl. No.: 16/703,691

(22) Filed: Dec. 4, 2019

(65) Prior Publication Data
US 2020/0189182 A1    Jun. 18, 2020

Related U.S. Application Data

(60) Provisional application No. 62/778,639, filed on Dec. 12, 2018.

(51) Int. Cl.
*B33Y 70/10* (2020.01)
*B29C 64/118* (2017.01)
(Continued)

(52) U.S. Cl.
CPC ............ *B29C 64/118* (2017.08); *A61L 27/44* (2013.01); *A61L 27/52* (2013.01); *A61L 27/56* (2013.01);
(Continued)

(58) Field of Classification Search
CPC .......... B33Y 70/10; A61L 27/44; A61L 27/52; A61L 27/56
See application file for complete search history.

(56) References Cited

U.S. PATENT DOCUMENTS 10,117,968 B2    11/2018  Lewis et al.
10,974,441 B2 *   4/2021  Huang ................... B33Y 70/00
(Continued)

*Primary Examiner* — Yung-Sheng M Tsui
(74) *Attorney, Agent, or Firm* — Alston & Bird LLP

(57) ABSTRACT

Described herein are apparatuses, systems, and methods for fabricating tissue constructs, such as by fabricating perfusable tissue constructs by embedding a sacrificial material into a composite matrix yield stress support bath. A composite matrix bath can include a microgel filler and a hydrogel precursor. An extrusion tip can be used for embedded printing of perfusable tissue constructs by disposing sacrificial material into the composite matrix bath while the extrusion tip travels along a predefined course through the composite matrix bath. This sacrificial material can be the printed tissue construct or can be removed to render the matrix bath a perfusable tissue construct. The composite matrix bath can include acellular or cell-laden hydrogels. The sacrificial material can include a salt and a physiological buffer or a non-cytotoxic porogen material. The hydrogel precursor can include at least one of gellan and gelatin. Cross-linking can be carried out chemically, thermally, enzymatically, or physically.

18 Claims, 10 Drawing Sheets

(51) Int. Cl.
  *B29C 64/40* (2017.01)
  *A61L 27/44* (2006.01)
  *A61L 27/56* (2006.01)
  *A61L 27/52* (2006.01)
  *B29K 105/00* (2006.01)
  *B29K 105/16* (2006.01)
  *B29L 31/40* (2006.01)

(52) U.S. Cl.
  CPC .............. *B29C 64/40* (2017.08); *B33Y 70/10* (2020.01); *B29K 2089/00* (2013.01); *B29K 2105/0061* (2013.01); *B29K 2105/16* (2013.01); *B29L 2031/40* (2013.01)

(56) References Cited

U.S. PATENT DOCUMENTS

2017/0368743 A1* 12/2017 Kang .................... B29C 64/393
2018/0230423 A1*  8/2018 O'Mahony ............ B33Y 40/00
2019/0010288 A1*  1/2019 Lee ..................... A61L 27/3813
2019/0134276 A1*  5/2019 Spiller ................. C09D 11/101
2020/0298487 A1*  9/2020 Devlin .................. B29C 64/255
2021/0031434 A1*  2/2021 Martinez ................ C12M 23/16

* cited by examiner

CROSS-LINKABLE MICROGEL COMPOSITE MATRIX BATH FOR EMBEDDED BIOPRINTING OF PERFUSABLE TISSUE CONSTRUCTS

CROSS-REFERENCE TO RELATED APPLICATIONS

This application claims priority to and the benefit of U.S. Provisional Patent Application Ser. No. 62/778,639, filed Dec. 12, 2018 and titled "Cross-Linkable Microgel Composite Matrix Bath for Embedded Bioprinting of Perfusable Tissue Constructs," the entire disclosure of which is hereby incorporated herein by reference in its entirety for all purposes.

BACKGROUND

Tissue engineering is a field which seeks to understand and model structural and functional features of living tissue, and to mimic features, mechanisms, and functionalities of the living tissue in engineered constructs. There are a variety of purposes for these engineered constructs, including but not limited to: mimicking healthy and disease states to better understand and treat diseases, modeling physiological responses for drug discovery and validation, and promoting regeneration of damaged tissue in vivo. As the need for such engineered constructs continues to grow and further applications are developed, more robust and versatile approaches for fabricating these engineered constructs are needed. Through applied effort, ingenuity, and innovation, solutions to improve such apparatuses, systems, and methods have been realized and are described in connection with embodiments of the present invention.

BRIEF SUMMARY

Described generally herein, according to at least some embodiments, are apparatuses, systems, and methods for fabricating engineered tissue constructs. For example, according to some embodiments, a method, along with the associated system and apparatus, are provided for additive manufacturing of tissue constructs by printing a build material into a support bath.

According to some embodiments described herein, a method is provided for embedded printing of perfusable tissue constructs, the method comprising: providing a composite matrix bath comprising a microgel filler and a hydrogel precursor; disposing, using an extrusion tip configured to travel along a predefined course through the composite matrix bath, a volume of a sacrificial material into the composite matrix bath, wherein the volume of sacrificial material disposed along the predefined course is retained within the composite matrix bath; allowing the volume of the sacrificial material to at least partially solidify; and removing the volume of the at least partially solidified sacrificial material from the composite matrix bath to form one or more voids substantially similar in volume and form factor to the volume of the at least partially solidified sacrificial material.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, a method such as that described above may further comprise cross-linking the hydrogel precursor to change one or more rheological properties of the composite matrix bath. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

According to other embodiments described herein, a system is provided for embedded printing of perfusable tissue constructs, the system comprising: a composite matrix bath comprising a microgel filler and a hydrogel precursor; a reservoir configured to store a supply of a sacrificial material; and an extrusion tip configured to travel along a predefined course through the composite matrix bath and dispose at various points along the predefined course the sacrificial material into the composite matrix bath. In some embodiments, the volume of sacrificial material disposed along the predefined course is retained within the composite matrix bath. In some embodiments, the volume of the sacrificial material, once disposed within the composite matrix bath, at least partially solidifies. In some embodiments, once the volume of the at least partially solidified sacrificial material is removed from the composite matrix bath, one or more voids are formed that are substantially similar in volume and form factor to the volume of the at least partially solidified sacrificial material.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, the hydrogel precursor is operable to be cross-linked to change one or more rheological properties of the composite matrix bath. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change, e.g., using transglutaminase.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

According to yet other embodiments described herein, a method is provided for embedded printing, the method comprising: preparing a composite matrix bath comprising a microgel filler and a hydrogel precursor; disposing, using an extrusion tip configured to travel along a predefined course through the composite matrix bath, a volume of a sacrificial material into the composite matrix bath, wherein the volume of sacrificial material disposed along the predefined course is retained within the composite matrix bath; allowing the volume of the sacrificial material to at least partially solidify; cross-linking, e.g., enzymatically cross-linking, the hydrogel precursor to change one or more rheological properties of the composite matrix bath; and terminating cross-linking by heating the composite matrix bath to a temperature greater than a temperature threshold.

In some embodiments, the sacrificial material comprises a salt and a physiological buffer or a non-cytotoxic porogen material, and the hydrogel precursor comprises at least one of gellan-containing microgels, gelatin-containing microgels, or other hydrogel-based biocompatible microgels. In some embodiments, the sacrificial material comprises alginate and phosphate buffered saline, the hydrogel precursor comprises gellan-based microgels and gelatin-based microgels, and the composite matrix bath further comprises calcium chloride, the calcium chloride operable to induce gelation of the printed sacrificial material.

In some embodiments, methods such as that describe above can further comprise removing the volume of the at least partially solidified sacrificial material from the composite matrix bath to form one or more voids substantially similar in volume and form factor to the volume of the at least partially solidified sacrificial material.

BRIEF DESCRIPTION OF THE DRAWINGS

Figure 1:
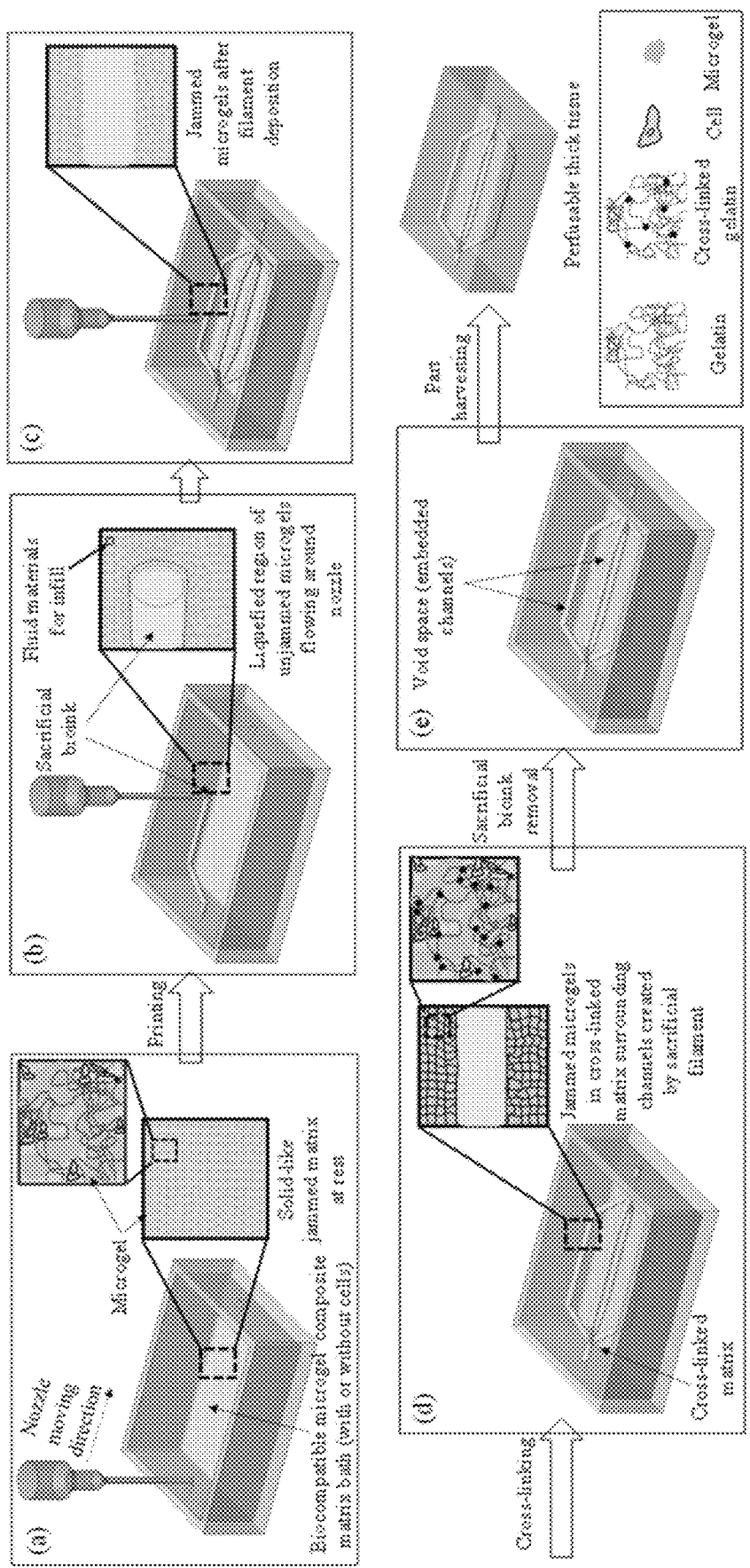
Figure 2:
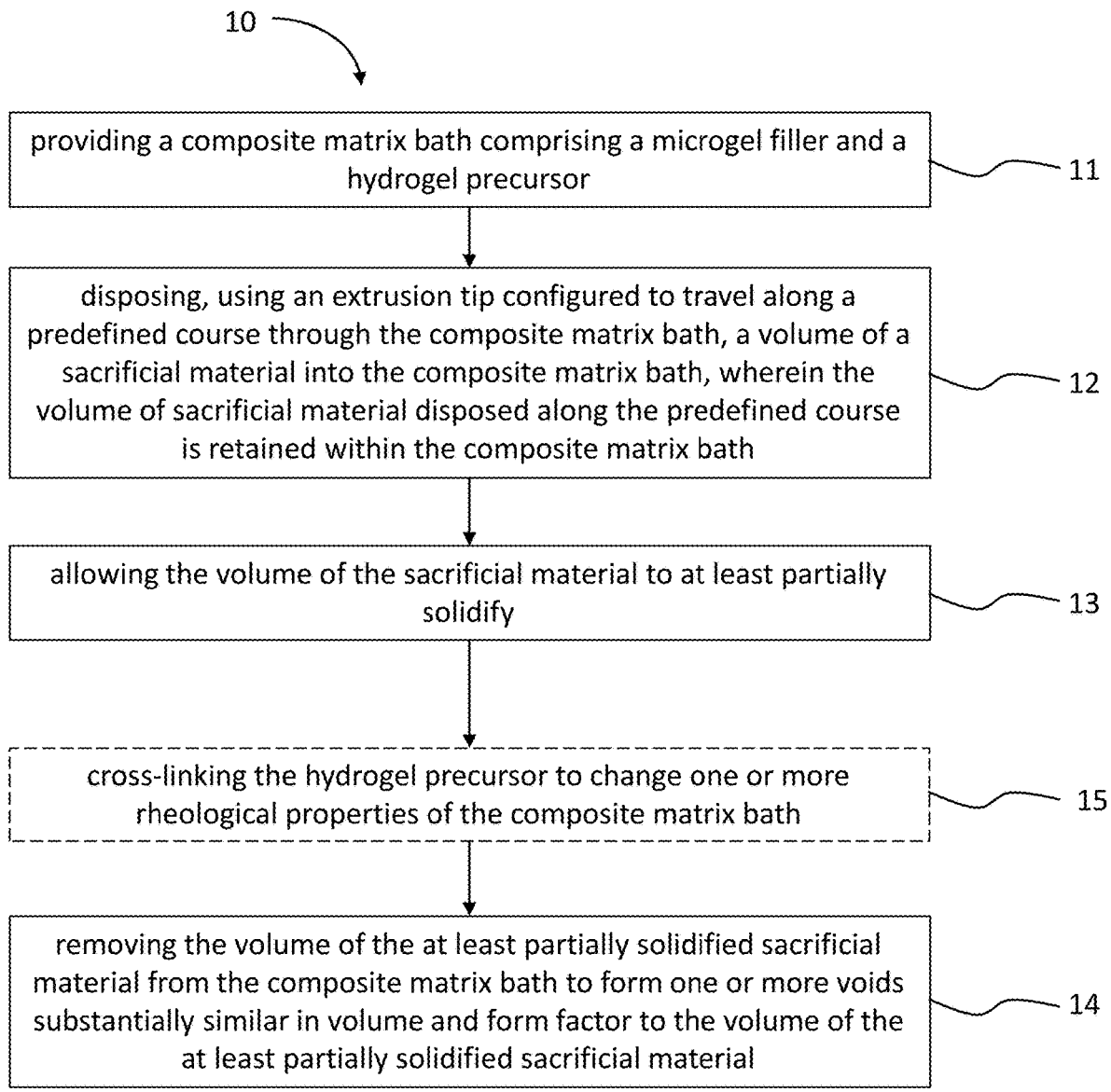
Figure 3:
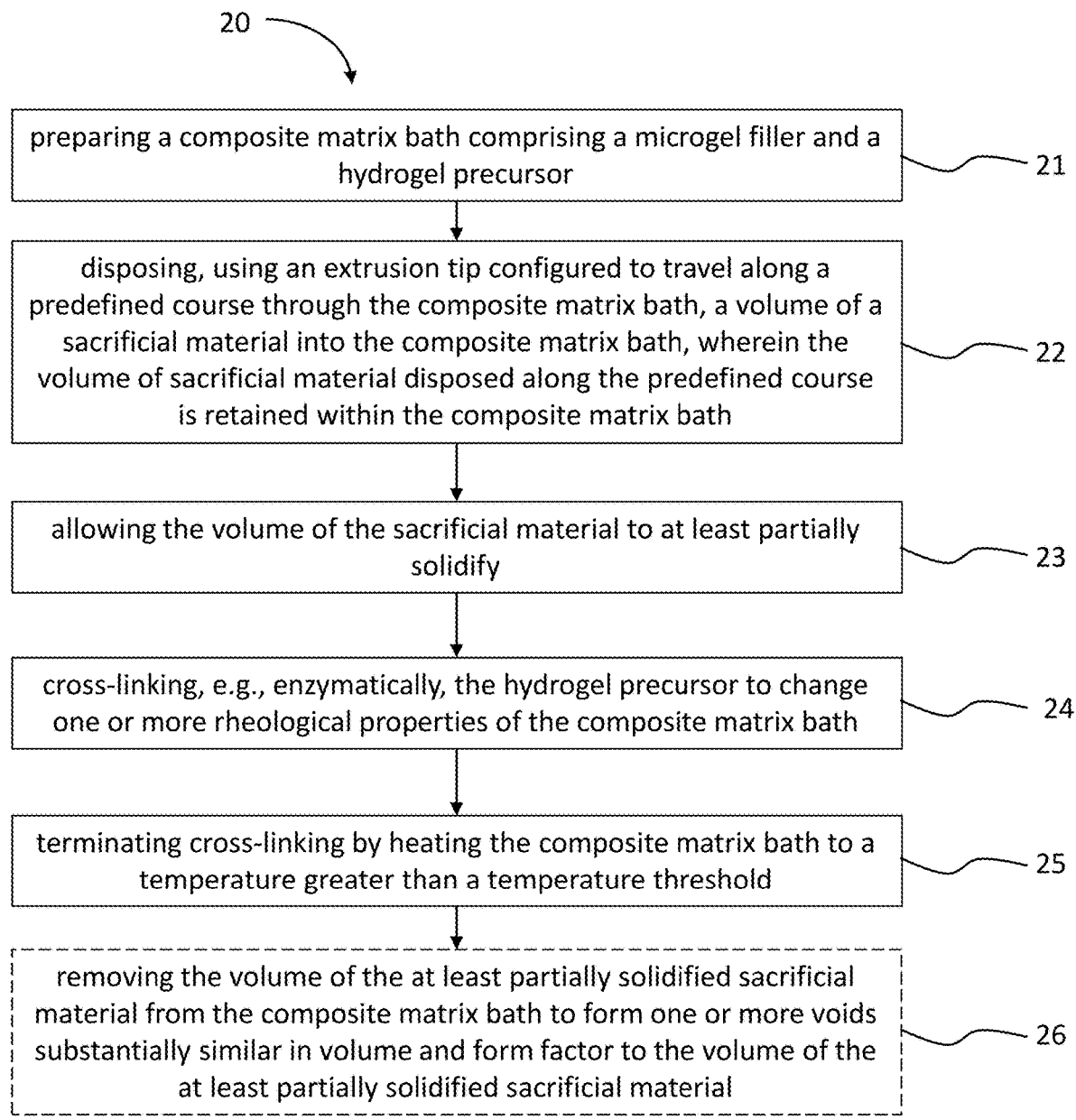
Figure 4:
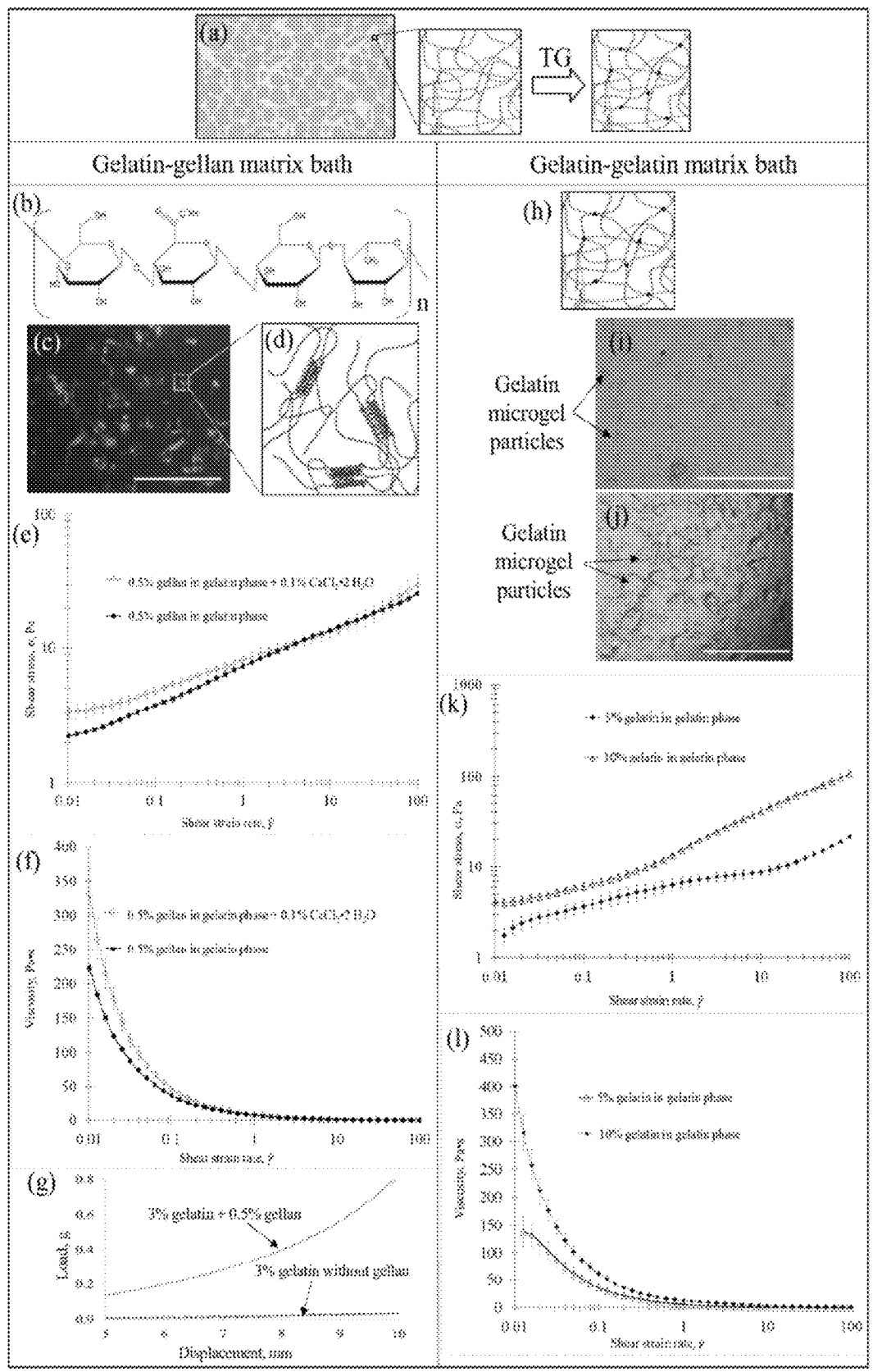
Figure 5:
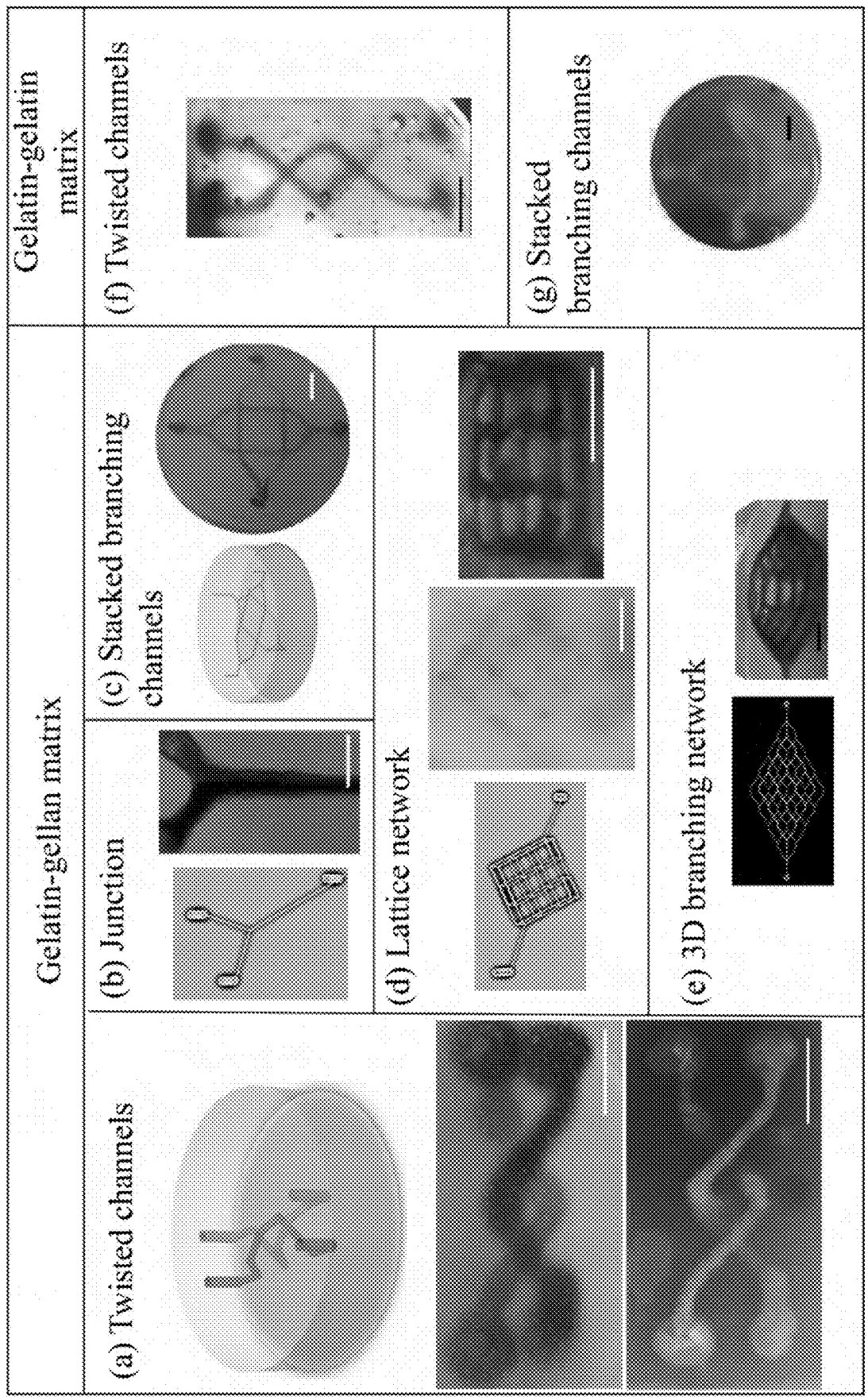
Figure 6:
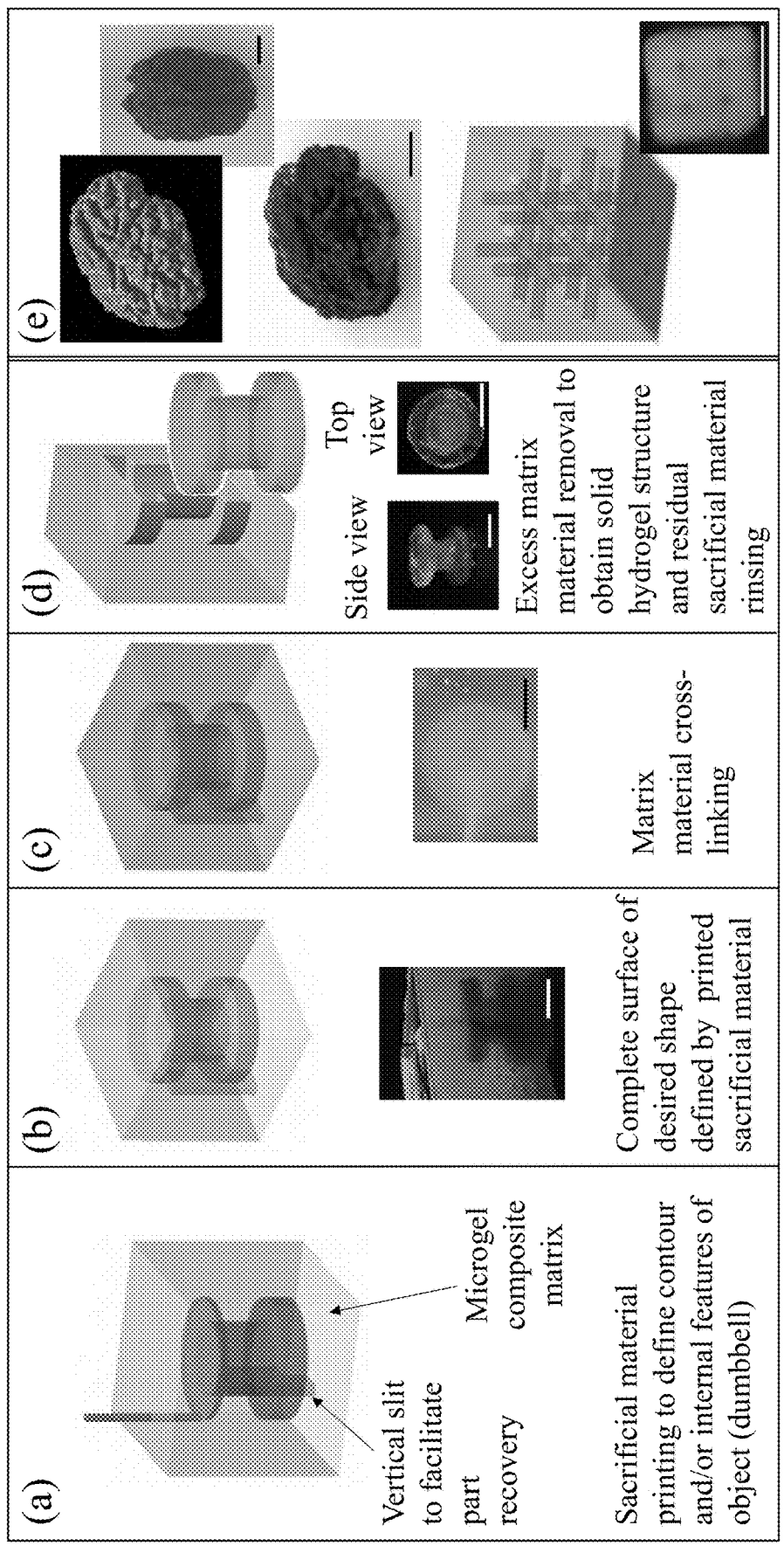
Figure 7:
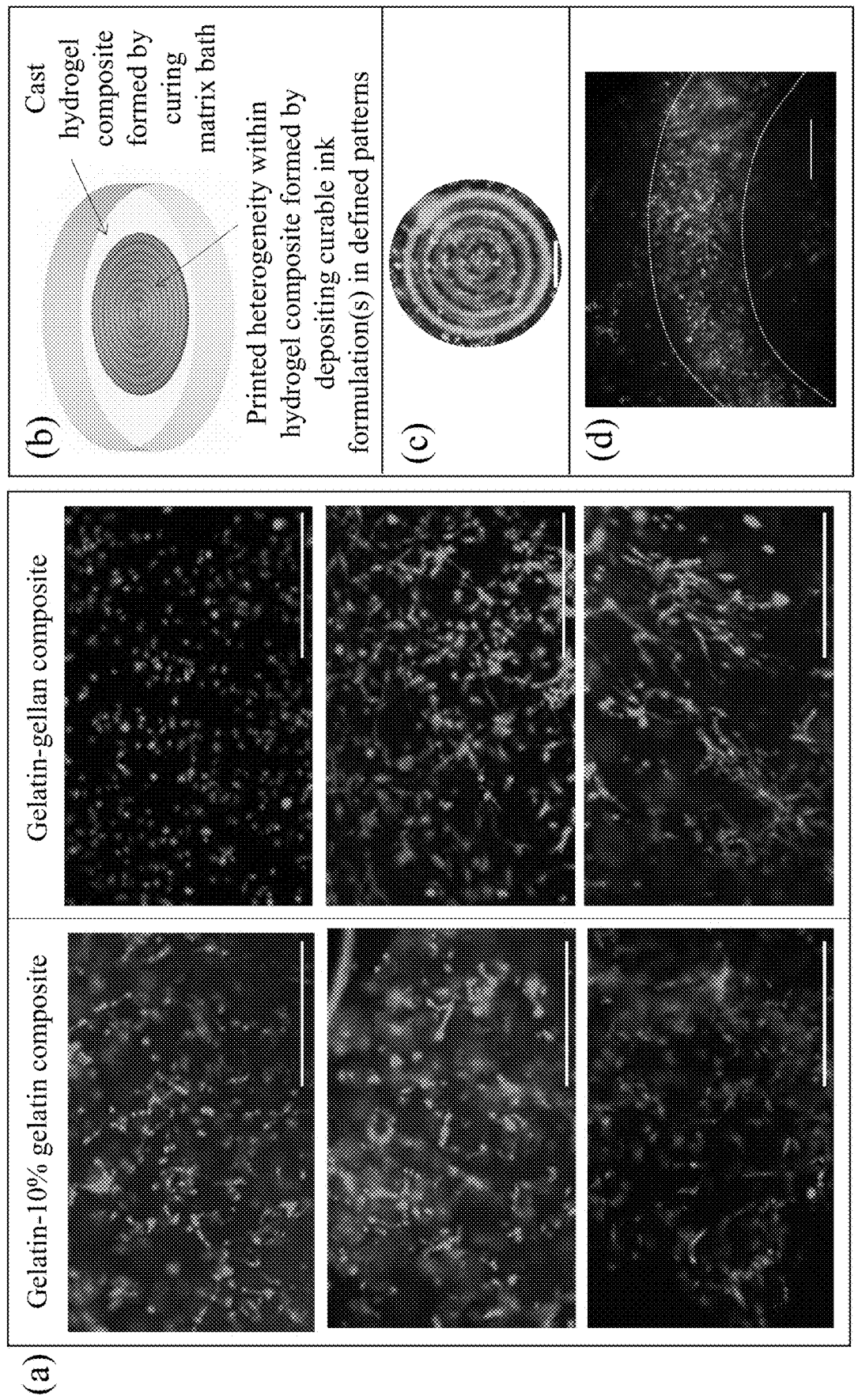
Figure 8:
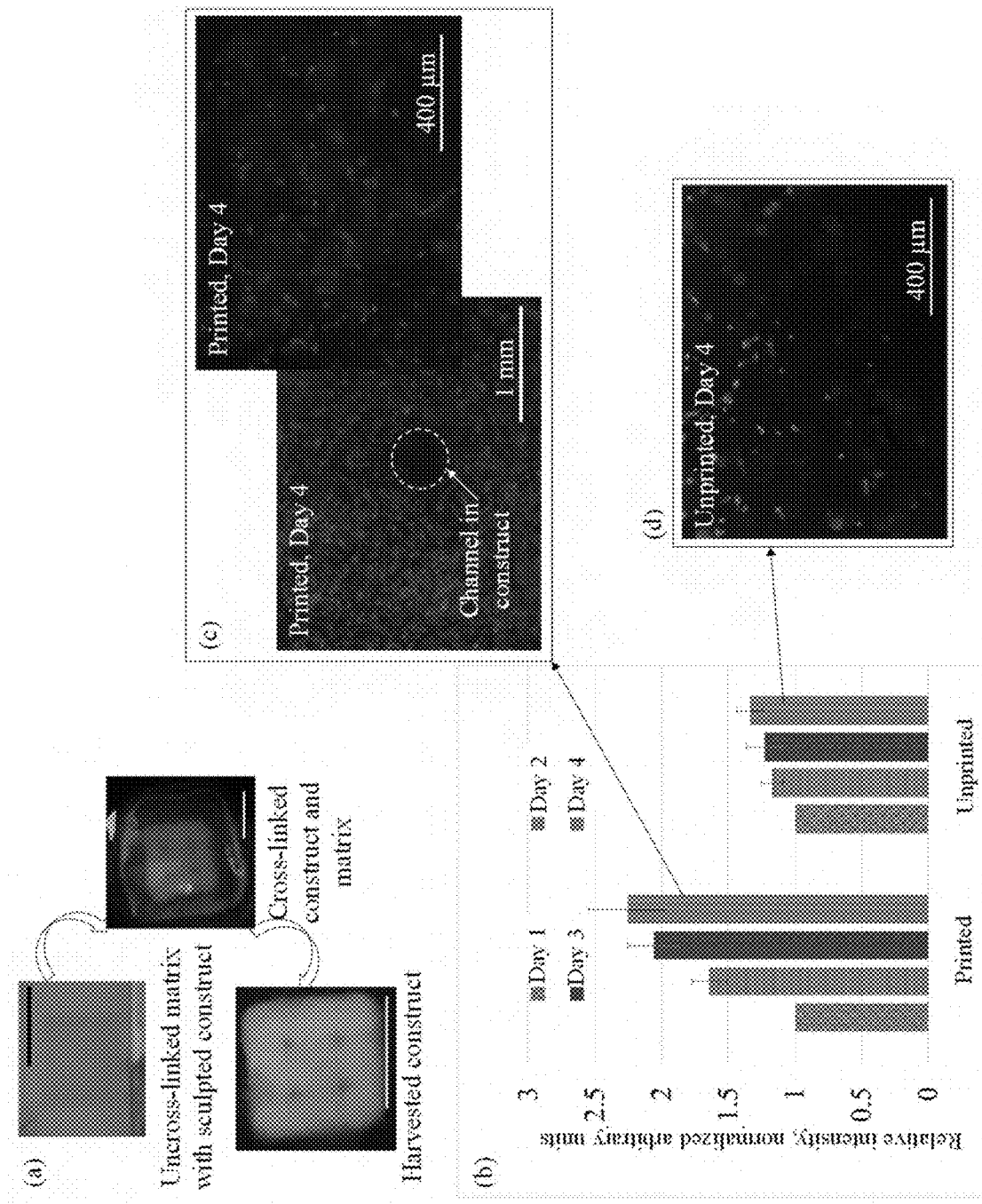
Figure 9:
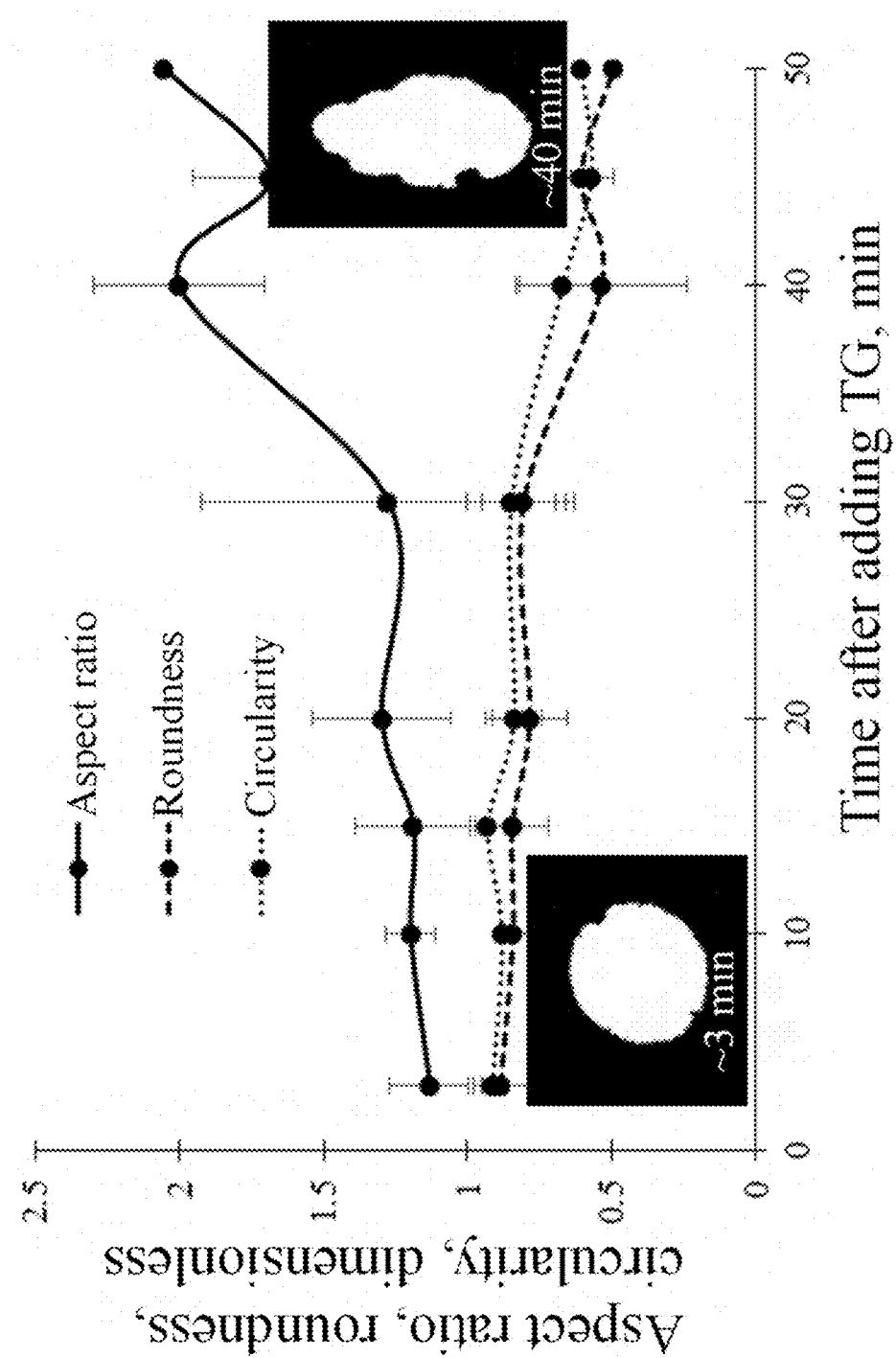
Figure 10:
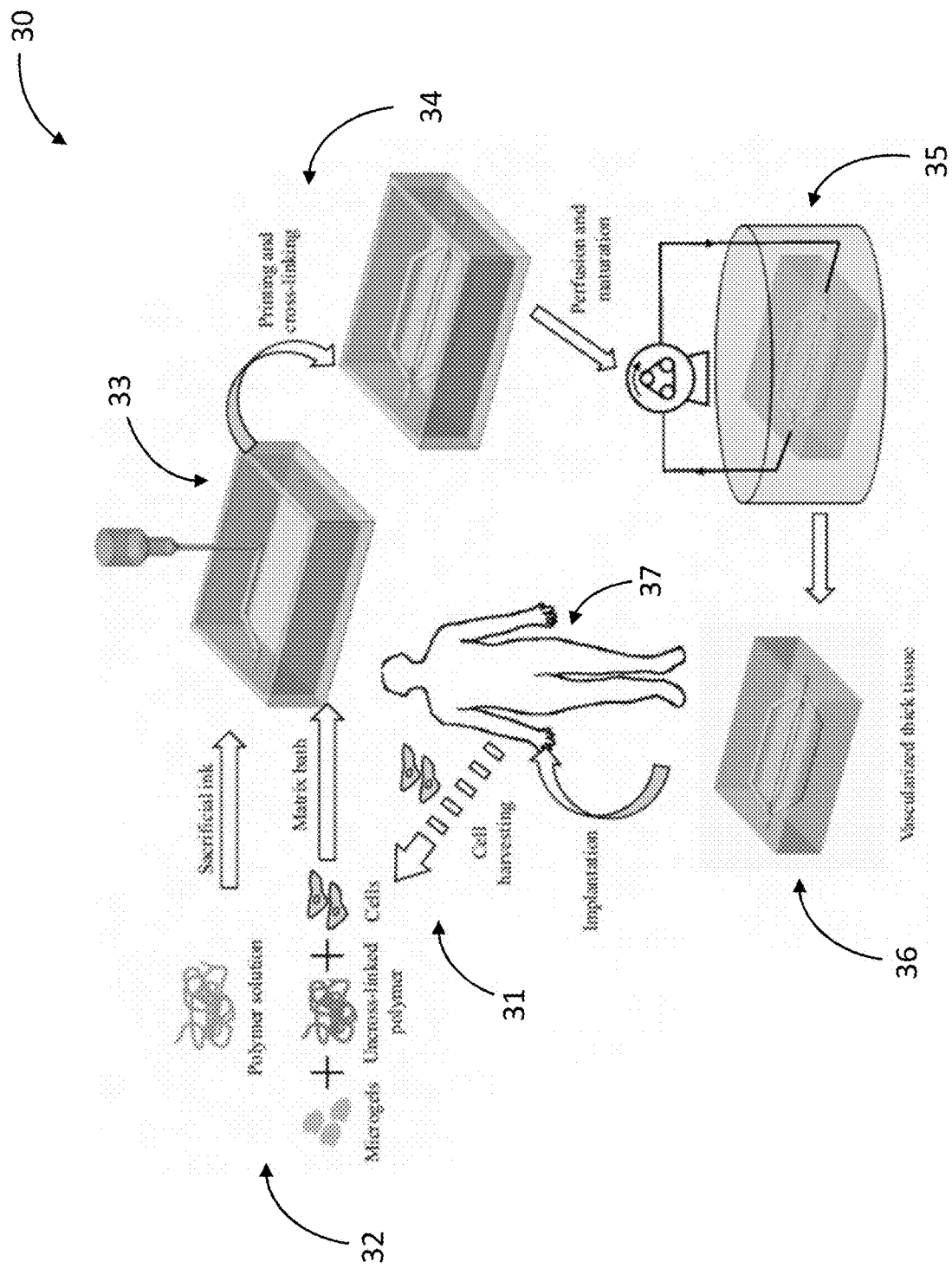

Having thus described the invention in general terms, reference will now be made to the accompanying drawings, which are not necessarily drawn to scale, and wherein:

FIG. 1 illustrates a process for printing tissue constructs in a matrix bath, according to an embodiment of the present disclosure;

FIG. 2 is a process flow diagram of a method for printing tissue constructs in a composite matrix bath, according to an embodiment of the present disclosure;

FIG. 3 is a process flow diagram of a method for printing tissue constructs in a composite matrix bath, according to an embodiment of the present disclosure;

FIG. 4 illustrates some of the possible compositions for a microgel composite matrix bath and mechanical properties thereof, according to some embodiments of the present disclosure; scale bars represent 1 mm;

FIG. 5 illustrates some of the possible printed internal structures and features for different microgel composite matrix bath compositions, according to some embodiments of the present disclosure; scale bars represent 5 mm;

FIG. 6 illustrates some of the possible printed solid objects sculpted using embedded surface printing, according to some embodiments of the present disclosure; scale bars represent 5 mm;

FIG. 7 provides fluorescence scans of living cells within various composite matrix formulations over time and illustrates patterning of heterogeneous cell populations within a gelatin-gelatin hydrogel composite disc; scale bars represent: 400 µm for Section (a), 5 mm for Section (c), and 500 µm for Section (d);

FIG. 8 provides images of some of the possible printed constructs, cell activity within those constructs, and living cell florescence images; scale bars represent: 5 mm unless otherwise marked;

FIG. 9 provides a graph of the effects of changing rheological properties on printed channel morphology, according to some embodiments of the present disclosure; and FIG. 10 illustrates a method for fabricating an implantable, perfusable thick tissue construct using cells harvested from the patient thereafter receiving the implanted tissue construct; according to an embodiment of the present disclosure.

Those in the art will understand that a number of variations may be made in the disclosed embodiments, all without departing from the scope of the present disclosure, which is defined solely by the appended claims.

DETAILED DESCRIPTION

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Tissue engineering is a field which seeks to recapitulate structural and functional features of living tissue in engineered constructs. There are a variety of purposes for these constructs: mimicking healthy and disease states to better understand diseases, modeling physiological responses for drug discovery and validation, and promoting regeneration of damaged tissue in vivo, to name a few. Additive manufacturing, or three-dimensional (3D) printing, has been shown, at least in some situations, to be a particularly useful tool for fabricating engineered tissue constructs. In some instances, the unique capacity of 3D printing techniques for rapid, customized fabrication with the potential for material heterogeneity and the capability to incorporate living cells without inflicting damage to the living cells may also be an important consideration for tissue construct design optimization and/or for patient-specific treatments, such as during translation of this technology to clinical applications. In terms of the clinical relevancy of such tissue engineering methods, it may be important to consider the capability of the method to fabricate perfusable thick tissues.

Fortunately, 3D printing can be utilized to fabricate perfusable thick tissues in two complementary ways: freeform fabrication in which the build material forms the final construct, or printing a sacrificial template to define features within a cast construct. Various approaches to print living cell-laden tubular structures or perfusable channels by freeform fabrication have been contemplated, including but not limited to ink jetting, laser printing, and bath-supported extrusion. However, while directly printing a perfusable thick construct may be, in some instances, a less complex procedure than printing a sacrificial material, direct printing of perfusable thick constructs is typically inefficient because the bulk ink material occupies most of the construct volume, the process may be slower, and the channel morphology is often not smooth enough and may also deteriorate due to the layer-by-layer nature of the direct printing process.

Alternatively, 3D printed templates made of a sacrificial material have been contemplated for generating channel networks within biological constructs to mimic vascularized thick tissues. There are at least two basic implementations of this strategy: casting a matrix material around a pre-printed sacrificial template (e.g., a printing-then-casting approach) or printing a sacrificial template within a matrix precursor in the mold cavity (e.g., a casting-then-printing approach, or the embedded printing approach). In general, after the sacrificial template is embedded in a matrix precursor material, the matrix can then be cured (e.g., gelled, cross-linked, polymerized, solidified, or otherwise modified in terms of rheological properties as to achieve sufficient yield stress support for the sacrificial material). The sacrificial material can then be liquefied to create voids in the desired configuration within the construct. The printing-then-casting process is compatible with a wide range of sacrificial and matrix materials, relatively simple to implement, and requires no specific material characteristics except that, in at least some instances, the sacrificial material may be or become at least partially soluble with regard to the composite matrix bath. However, there can be some limitations to this approach with regard to the complexity of 3D self-supporting sacrificial templates. In some instances, more complicated 3D self-supporting templates may be difficult to print for some applications, and sacrificial templates can be damaged during composite matrix casting.

In the casting-then-printing/embedded printing approach, "sacrificial material" (also known herein as "build material" "ink," or "sacrificial ink") can be patterned within the matrix precursor, an approach which has been found to be effective for many acellular and cellular applications. This approach may allow for simultaneous control of the template architecture and placement within the overall construct while minimizing handling since the construct is formed in a single step and can be formed within a fixture. While this approach is attractive for at least these reasons, the casting-then-printing approach sometimes requires that the matrix have special rheological properties in order to retain the desired arrangement of sacrificial materials. In some embodiments, matrix materials can/should be yield stress materials for embedded printing and can/should be cross-linkable to form bulk solids or gels after the embedded pattern is complete. As described herein, yield stress materials are structured or complex fluids which behave as elastic solids at rest but transition to liquid-like, often shear thinning, behavior when the applied shear stress exceeds a threshold; this material specific threshold stress is designated the yield stress. This type of rheological behavior may be a result of micro- and/or nano-scale structural units or features within the fluid which can be rearranged for flow to take place; the yield stress may be a result of the threshold energy input required to disrupt the static structure.

Unfortunately, there are not many suitable single hydrogel matrix materials that can be used for such embedded printing processes. Further, pluronic-based hydrogels and specially designed guest-host hydrogels are generally unsuitable for hosting cell cultures and guest-host hydrogels also typically lack long-term stability.

General Overview

Provided herein are various embodiments of a method, apparatus, and system for forming a cross-linkable microgel composite matrix bath. Also provided herein are various embodiments of a method, apparatus, and system for embedded bioprinting of perfusable tissue constructs using a cross-linkable microgel composite matrix bath.

Tissue engineering approaches are described for generating, e.g., cell-laden tissue analogs with a wide range of internal and external physical features, including but not limited to perfusable channels, cavities, custom shapes, and spatially varying material and/or cell compositions. According to some embodiments, a versatile embedded printing method is provided for creating custom biomedical acellular and/or cell-laden hydrogel constructs by utilizing a biocompatible microgel composite matrix bath. In some embodiments, a sacrificial material can be extruded, injected, printed, patterned, or otherwise disposed within a biocompatible hydrogel precursor matrix bath, e.g., using extrusion printing, to create three-dimensional (3D) features within the biocompatible hydrogel precursor matrix bath.

In some embodiments, after printing, the matrix bath can be cross-linked, and the sacrificial material is flushed away to create perfusable channels within the bulk composite hydrogel matrix. According to some embodiments, the matrix bath material can be or comprise a composite consisting of jammed cross-linked hydrogel microparticles (microgels) to control rheology during fabrication along with a fluid hydrogel precursor, which is cross-linked after fabrication to form the continuous phase of the composite hydrogel. According to some embodiments, for example, an embedded printing method is provided in which gellan or enzymatically cross-linked gelatin microgels are utilized with a continuous gelatin hydrogel precursor solution to make the composite matrix bath, and the composite hydrogel matrix is formed by enzymatically cross-linking the continuous gelatin phase after printing is complete. A variety of features including but not limited to discrete channels, junctions, networks, and external contours can be printed for demonstration, showing that a wide range of arbitrary and intricate internal and external features can be readily printed using some or all of the fabrication approaches described herein.

In some embodiments, cell-laden constructs with printed features are also provided. In some embodiments, a microgel composite hydrogel matrix may support cell activity, and printed channels therein may enhance proliferation compared to solid constructs, even for a static culture. According to some embodiments, the method for fabricating bulk 3D hydrogel constructs may enable more rapid, reproducible production of customized cell-laden bulk hydrogel thick tissue analogues on demand as compared to other contemplated and compared approaches. In addition, at least some of the approaches described herein may be used alternatively to fabricate, e.g., by embedded printing in the composite matrix bath, a solid object for which external contours are sculpted by discarding excess composite hydrogel matrix after printing and cross-linking.

Embodiments of the present application disclose the use of biocompatible microgel particles as fillers in a continuous cross-linkable hydrogel precursor phase to prepare composite matrix bath materials suitable for embedded printing. With this, the goal is to design a cytocompatible composite such that it retains the yield stress properties of the jammed microgel filler material to enable stable embedded pattern formation within a continuous curable matrix bath material. Thus, the entire construct matrix can be stabilized after fabrication for subsequent removal of the sacrificial ink and maturation of engineered tissues. This design approach has additional benefits as follows. Composite materials offer more tunable mechanical and chemical properties to better mimic tissue properties since both filler and continuous phase can be adjusted. Other features may be added to either component as well: encapsulated soluble factors to direct cell behavior and chemical functionalities to enable controlled or cell-mediated degradation are just a couple of the possibilities. Yield stress materials also prevent particle (cell) sedimentation, enabling consistent cell distribution throughout the construct even if the gel formation process is slow. Finally, cells and continuous matrix material form an interconnected network around filler particles, which increases the effective local cell density and promotes cellular interactions. Similar microgel-reinforced hydrogels have been found to be superior to either the pure matrix material or a double network comprised of the two polymers for engineered tissue applications; fabrication is more convenient, properties easier to adjust, and cells are more functional in the microgel composites. If the filler is degradable, the maturing tissue can eventually fill the voids left behind; if it is simply inert and biocompatible, then it provides extra volume to the tissue construct without consuming additional nutrients or producing waste, which may be advantageous in clinical soft tissue repair. The microgel composite matrix bath-based embedded printing approach therefore simultaneously addresses two major concerns in tissue engineering: achieving physiological cell density and perfusing engineered constructs. The matrix bath material design intrinsically elevates the local cell density by a factor of approximately 10, assuming that the microgels occupy 90% of the construct volume. In addition, the ability to print channels within bulk constructs enables fabrication of large-scale perfusable tissue analogues using readily available materials and equipment.

Exemplary Method(s)

Referring now to FIG. 1, a method, according to an embodiment, is provided for embedded printing. As illustrated in FIG. 1, a reservoir can be filled with a matrix bath material. In some embodiments, the matrix bath material may behave as a solid, e.g., when at rest. For some embodiments of the present application, the composite matrix bath may consist of jammed microgels (e.g., gellan-containing, gellan-based, gelatin-containing, and/or gelatin-based microgels) as a filler to adjust rheology and a hydrogel precursor (gelatin-based) as a continuous matrix, as illustrated in box (a) of FIG. 1. The terms "gellan-based" and "gellan-containing" are used interchangeably throughout this disclosure to refer to a composition containing any amount of gellan. Likewise, the terms "gelatin-containing" and "gelating-based" are also used interchangeably throughout this disclosure to refer to a composition containing any amount of gelatin. As such, any use of the terms "gellan-based" or "gelatin-containing" should not be taken as meaning that the described composition comprises a majority of either of the respective components.

In some embodiments, to create features in the matrix bath, an extrusion tip is inserted into the uncured matrix bath material so that it can deposit sacrificial material as it travels along one or more designed paths in two dimensions (e.g., in the x and y directions) or in three dimensions (e.g., in the x, y, and z directions) within the printing reservoir, as illustrated in box (b) of FIG. 1. In some embodiments, as the extrusion tip travels through the matrix bath material, the bulk matrix bath material may partially or fully liquefy as microgels deform and slide past one another, as shown in the inset within box (b) of FIG. 1. Without wishing to be bound by any particular theory, this liquefied region may allow sacrificial ink to flow out of the extrusion tip. As the tip moves away, the microgels may revert to a jammed solid-like configuration and the sacrificial material may be trapped in the portion of the matrix bath material that at least partially liquified and which subsequently reverted to the jammed solid-like configuration, as shown in box (c) of FIG. 1. In some embodiments, as shown in box (d) of FIG. 1, the gelation process may then be complete. In some embodiments, once the gelation process is complete, the sacrificial material may then be removed to create one or more void spaces or one or more channels surrounded by the cross-linked composite hydrogel matrix, as illustrated in box (e) of FIG. 1.

Referring now to FIG. 2, a method 10 is provided for embedded printing of perfusable tissue constructs, the method comprising: providing a composite matrix bath comprising a microgel filler and a hydrogel precursor, at 11; disposing, using an extrusion tip configured to travel along a predefined course through the composite matrix bath, a volume of a sacrificial material into the composite matrix bath, wherein the volume of sacrificial material disposed along the predefined course is retained within the composite matrix bath, at 12; allowing the volume of the sacrificial material to at least partially solidify, at 13; and removing the volume of the at least partially solidified sacrificial material from the composite matrix bath to form one or more voids substantially similar in volume and form factor to the volume of the at least partially solidified sacrificial material, at 14.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, the method 10 described above may, optionally, further comprise cross-linking the hydrogel precursor to change one or more rheological properties of the composite matrix bath, at 15. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change, e.g., using transglutaminase.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

Referring now to FIG. 3, a method 20 is provided for embedded printing, the method comprising: preparing a composite matrix bath comprising a microgel filler and a hydrogel precursor; disposing, using an extrusion tip configured to travel along a predefined course through the composite matrix bath, a volume of a sacrificial material into the composite matrix bath, wherein the volume of sacrificial material disposed along the predefined course is retained within the composite matrix bath; allowing the volume of the sacrificial material to at least partially solidify; cross-linking, e.g., enzymatically cross-linking, the hydrogel precursor to change one or more rheological properties of the composite matrix bath; and terminating cross-linking by heating the composite matrix bath to a temperature greater than a temperature threshold.

In some embodiments, the sacrificial material comprises a salt and a physiological buffer or a non-cytotoxic porogen material, and the hydrogel precursor comprises at least one of gellan-containing microgels, gelatin-containing microgels, or other hydrogel-based biocompatible microgels. In some embodiments, the sacrificial material comprises alginate and phosphate buffered saline, the hydrogel precursor comprises gellan-based microgels and gelatin-based microgels, and the composite matrix bath further comprises calcium chloride, the calcium chloride operable to induce gelation of the printed sacrificial material.

In some embodiments, methods such as that describe above can further comprise removing the volume of the at least partially solidified sacrificial material from the composite matrix bath to form one or more voids substantially similar in volume and form factor to the volume of the at least partially solidified sacrificial material.

In some embodiments, an apparatus or system can be provided for carrying out some or all of the method 10 or the method 20, as described herein. For instance, according to some embodiments, a system is provided for embedded printing of perfusable tissue constructs, the system comprising: a composite matrix bath comprising a microgel filler and a hydrogel precursor; a reservoir configured to store a supply of a sacrificial material; and an extrusion tip configured to travel along a predefined course through the composite matrix bath and dispose at various points along the predefined course the sacrificial material into the composite matrix bath. In some embodiments, the volume of sacrificial material disposed along the predefined course is retained within the composite matrix bath. In some embodiments, the volume of the sacrificial material, once disposed within the composite matrix bath, at least partially solidifies. In some embodiments, once the volume of the at least partially solidified sacrificial material is removed from the composite matrix bath, one or more voids are formed that are substantially similar in volume and form factor to the volume of the at least partially solidified sacrificial material.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, the hydrogel precursor is operable to be cross-linked to change one or more rheological properties of the composite matrix bath. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change, e.g., using transglutaminase.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

Exemplary Composition(s)

FIG. 4 illustrates some of the disclosed compositional embodiments of the microgel composite matrix bath and various mechanical properties associated with these microgel composite matrix bath compositions. Section (a) of FIG. 4 illustrates a possible composite matrix in which microgel particles (blue) are disposed within a continuous gelatin matrix (beige). The inset illustrated with in Section (a) illustrates gelatin in solution and after cross-linking with an enzyme, such as transglutaminase (TG). Section (b) of FIG. 4 provides the chemical structure of gellan. Section (c) of FIG. 4 provides an image of gellan microgel particles. Section (d) of FIG. 4 illustrates, according to one embodiment, gellan gelation by aggregation of helices. Section (e) of FIG. 4 provides experimental results (shear stress vs. shear strain rate of various composite matrix materials) related to the rheology of gelatin-gellan composite matrix bath materials to quantify the yield stress behavior at 37° C. Section (f) of FIG. 4 provides experimental results (viscosity vs. shear strain rate of various composite matrix materials) related to the rheology of gelatin-gellan composite matrix bath materials to quantify the yield stress behavior at 37° C. Section (g) of FIG. 4 provides a chart illustrating the mechanical behavior of gelatin (without gellan) vs. a gelatin-gellan microgel composite as load vs. displacement. Section (h) of FIG. 4 provides a schematic of covalently cross-linked gelatin microgel. Section (i) of FIG. 4 provides an optical micrograph of a 5% w/v gelatin microgel. Section (j) of FIG. 4 provides an optical micrograph of a 10% w/v gelatin microgel. Section (k) of FIG. 4 provides a chart comparing shear stress vs. shear strain rate for a gelatin-gelatin composite matrix bath to quantify the yield stress behavior at 37° C. (Scale bars: 1 mm). Section (1) of FIG. 4 provides a chart comparing viscosity vs. shear strain rate for a gelatin-gelatin composite matrix bath to quantify the yield stress behavior at 37° C. (Scale bars: 1 mm).

In some embodiments, microgel-based composite matrix bath formulations, e.g., those that are made of microgel filler particles in a continuous cross-linkable hydrogel precursor phase, can be designed or engineered to have, for instance, appropriate rheological properties, biocompatibility, working time, and mechanical properties. By way of example only, two of the contemplated microgel materials are gellan and gelatin. However, other microgel materials are also contemplated and are within the scope of the present disclosure. For instance, other contemplated materials include but are not limited to 4-arm poly ethylene glycol-succinimidyl glutaramide (PEG-NHS), (NHSA)-microgels, poly(2-hydroxyethyl acrylate-co-poly(ethylene glycol) diacrylate) hydrogels, agar, agarose, chitosan, chitin, alginate, whey protein, collagen, cellulose, carboxymethyl cellulose, cellulose nanocrystals, gelatin methacrylate, hyaluronic acid-based microgels, poly(methyl methacrylate-co-methacrylic acid-co-ethylene glycol dimethacrylate) microgels (optionally, functionalized with glycidyl methacrylate), poly(N-isopropylacrylamide) (pNIPAm) microgels, poly(N-isopropylmethacrylamide) (pNIPMAm) microgels, pNIPAm microgels cross-linked with either 1% or 10% mol N,N'-methylenebis(acrylamide) (BIS), microgels comprising either pNIPAm or pNIPMAm and synthesized with 10 mol % of degradable cross-linker (1,2-dihydroxyethylene)bis (acrylamide) (DHEA), PNIPMAm microgels with 2% mol acrylic acid (AAc) and operable to be cross-linked with 2% mol N,O-dimethacryloyl hydroxylamine (DMHA), microgels comprising one or more selected from among N-isopropylacrylamide, N-isopropyl-methacrylamide, N,N-diethylacrylamide, N-vinylcaprolactam, N,N-methylenebisacrylamide, 1-vinylimidazole, acrylic acid, methacrylic acid, 3-(N,N-dimethylamino) propylmethacrylamide, N-(3-aminopropyl) methacrylamide, 2-(dimethyl maleinimido)-

N-ethylacrylamide, redox-active monomers, light-active azobenzene monomers, combination or variations thereof, and the like.

In some embodiments, the microgel particles are formed as a dispersion by shearing or fragmenting hydrogels after gelation. In some embodiments, microgel particles in a dispersion, e.g., after gelation, can have a yield stress since they are jammed systems. In some embodiments, the yield stress may be due, at least in part, to the threshold energy required to make the microgels deform and slide past one another. In some embodiments, for the continuous phase of composite matrix bath material formulations, unmodified gelatin may be used. In some embodiments, the continuous phase can be cross-linked using an enzyme, such as but not limited to transglutaminase (TG), to form stable constructs after printing is complete.

As described herein, gellan is a linear anionic microbial polysaccharide which is contemplated herein for use in a variety of fields and applications, for example in tissue engineering, drug delivery, food science, or the like. In some embodiments, a tetrasaccharide sequence such as those including two β-D-glucose residues, one β-D-glucuronate residue, and/or one α-L-rhamnose residue can be used as a repeat unit for forming gellan, as shown in FIG. 4, Section (a). In some embodiments, native gellan biopolymer can contain acyl groups which are removed to produce the widely-used low acyl version of the biopolymer. Without wishing to be bound by any particular theory or mechanism, at high temperatures, gellan molecules may act or exist as random coils in aqueous solution. In some embodiments, when gellan molecules are cooled, at least some regions of the polymer may adopt a helical conformation and aggregate to form junction zones, resulting in a bulk hydrogel by physical gel formation, for instance as shown in FIG. 4, Section (b). In some embodiments, low acyl gellan may form clear, brittle hydrogels which can be easily processed into microgels. Although low-acyl gellan can form stiff gels without added salt, the gel properties can be modulated by changing the concentration and composition of added ions. Hydrogels formed in the presence of monovalent salts are often thermoreversible, while divalent salts may increase, or significantly increase, thermal stability and, at least in some instances, make the gels essentially irreversible. As disclosed herein, gellan can be prepared at a concentration of 0.5% w/v in a physiological buffer or a non-cytotoxic porogen material, such as a phosphate buffered saline (PBS) buffer, to prevent osmotic shock to printed cells, stabilize the pH, and match the ionic strength of the ink formulations to minimize swelling. In some embodiments, bulk gels can be fragmented by passing the bulk gels through a stainless steel mesh, resulting in a smoothly flowing yield stress fluid. According to light scattering analyses and microscopic examination, such dispersions may exhibit irregular microgel particles and particle aggregates with typical dimensions of 20-100 μm (average diameter 50±34 μm based on light scattering data, and average aspect ratio 1.6 based on image analysis), as shown in FIG. 4, Section (c). In some embodiments, the gellan concentration can be fixed at or about 0.5% w/v, a concentration which may, at least in some embodiments, provide suitable yield stress and shear thinning rheology for the printing process, as shown in FIG. 4, Sections (e-f).

In some embodiments, the versatility of the disclosed approach can be seen as gelatin microgels are also described. Gelatin is a protein derived from collagen. Without wishing to be bound by any particular theory or mechanism, gelatin may form physical hydrogels via physical interactions between helical regions of the protein. However, in some embodiments, at temperatures above approximately 35° C., the hydrogel often liquefies as helical regions become random coils. According to some embodiments, in order to increase physiological stability of gelatin-containing microgels, gelatin can be cross-linked using a variety of chemical cross-linking agents, such as by using the enzyme TG as a cross-linking agent since such approaches typically produce transparent, non-toxic, stable, transparent, degradable, biocompatible structures suitable for in vitro and in vivo applications. Without wishing to be bound by any particular theory or mechanism, TG is an enzyme which may covalently link gelatin molecules to one another, forming a cross-linked network. Enzymes are attractive tools for tissue engineering since they are biological catalysts which are usually highly active under physiological conditions with high specificity and low toxicity. Transglutaminases (TGs) are a family of enzymes which form covalent linkages between protein molecules. Transglutaminases are typically non-toxic, biodegradable, cytocompatible, and do not introduce toxic residues or byproducts (except for trace amounts of ammonia which may be processed through normal metabolic pathways active in cells). Because it can be used to form physiologically stable cell-laden gel constructs from native gelatin, TG is described in many embodiments presented herein, however many other enzymes are contemplated and many other strategies for forming physiologically stable gelatin hydrogels such as gelatin methacrylate (GelMA) can be used and would be understood by one of ordinary skill in the art, in view of the present disclosure, to be within the scope of this disclosure. However, some strategies for forming physiologically stable gelatin hydrogels may require chemical modification of native gelatin to introduce the functional groups necessary for controlled physical or chemical hydrogel formation. While such modification may provide for increased control of hydrogel formation and properties, it can also significantly complicate the material preparation process since the native protein often must be modified and purified before use. Also, in some embodiments, residual reactants from the modification process, the functional groups themselves, initiators or catalysts, and/or the stimuli required to form a hydrogel from the modified gelatin may negatively impact encapsulated or seeded cells. For these reasons, native gelatin is recommended for use where possible to avoid these complications and make the process feasible in a wide range of facilities where extensive material modification may not be possible or convenient. That being said, other enzymes and/or approaches for forming physiologically stable gelatin hydrogels (or any other hydrogel or microgel disclosed herein) can be used without departing from the scope of this disclosure. Additionally, there are circumstances and instances in which native gelatin would not be the recommended choice for forming stable hydrogels. In some embodiments, the gelation time can be altered by changing the enzyme concentration without strongly affecting the final gel properties since the enzyme continues to create cross-links until no more active sites are available. Alternatively, in some embodiments, enzymatic cross-linking can be terminated by heat inactivation of the enzyme at some defined time point or once the material being cross-linked reaches a particular rheological property, which can produce cross-linked gels with intermediate rheological properties. Covalently cross-linked gelatin, like gellan, can be processed to form jammed microgel dispersions which are yield stress fluids. Thermally cross-linked gelatin microgels are also possible and are contemplated as viable options for the sacrificial support bath material for 3D printing and/or as part of the cross-linkable matrix bath.

In some embodiments, various gelatin concentrations, such as 5% and 10% w/v in PBS, can be utilized to prepare microgels from bulk gels cross-linked using, e.g., 0.5% and 1% w/v TG, respectively. In some embodiments, crosslinking for preparing microgels from bulk gels can be carried out for a period of about 4 hr at a temperature of about 37° C. For some example microgels that were prepared, similar particle size distributions (260±200 µm particle dimensions for 10% w/v gelatin and 125±100 µm particles for 5% w/v gelatin based on light scattering data) and morphologies were observed for both 5% and 10% w/v gelatin concentrations. Compared to gellan, at least in some embodiments, the gelatin particles appear to be rougher with generally lower aspect ratios (average aspect ratio 1.4 for both gelatin concentrations while 1.6 for gellan based on image analysis). Without wishing to be bound by any particular theory or mechanism, this may be attributed to the tearing and agitation during the blending process to produce gelatin microgels as well as the higher elasticity of the gelatin bulk gels which causes them to tear rather than shatter during fragmentation.

In some embodiments, the continuous phase of the composite matrix bath material may comprise soluble gelatin, which can be cross-linked using TG. In some embodiments, soluble gelatin can be compatible with both gellan and gelatin microgels, provided that the TG within the gelatin microgels is deactivated prior to mixing. According to some embodiments, if gelatin microgels containing residual active TG are utilized, the mixture may begin to gel quickly or even immediately, meaning that use of such rapidly gelling microgels is possible but possibly less convenient. As noted above, the gelation time can be altered by changing the enzyme concentration without strongly affecting the final gel properties since the enzyme continues to create cross-links until no more active sites are available. In instances in which the particular materials selected provide for a long gelation time, printing can be completed after mixing the matrix with the enzyme, allowing for formation of a homogeneously cross-linked construct. However, culture media components may deactivate TG, so for cell-laden constructs the cross-linking process may terminate when the cross-linking construct is immersed in or perfused with the culture media. As a result, the mechanical and chemical properties of cell-laden constructs may be more sensitive to the specific fabrication process and matrix bath formulation than acellular structures in which enzymatic cross-linking consumes all possible active sites over time.

Other routes to physiologically-stable gelatin hydrogels often rely on external stimuli such as ultraviolet (UV) irradiation of chemically modified gelatin or chemical cross-linking agents which are consumed during the cross-linking process. Irradiation is intrinsically inhomogeneous for thick constructs since the surface shields the interior, while cross-linking agents couple gel strength to cross-linker concentration so that slowing the cross-linking process inevitably means weakening the final construct. Microgels comprising combinations of gellan and gelatin are also described herein. Without wishing to be bound by any particular theory or mechanism, gellan and/or gelatin are biopolymers that may participate in hydrogen bonding and dipole-dipole interactions. For instance, in some embodiments positively charged amino acids in gelatin may also interact ionically with the negatively charged carboxylate functional groups in gellan. Without wishing to be bound by any particular theory or mechanism, such a reaction between gelatin and gellan may result in a strong interphase between matrix and filler and a structurally sound composite after gelation. Since the gellan is in the form of pre-gelled microgels, the microstructure is fixed and does not evolve over time, as it might if both gellan and gelatin were in solution simultaneously. According to some embodiments, there is a tendency for fluidic gelatin-gellan mixtures to phase separate under physiological conditions, which implies that the dissolved gelatin remains localized in the space between gellan microgels rather than infiltrating them since gellan-gellan and gelatin-gelatin interactions are favored over gelatin-gellan interactions.

According to some embodiments, the disclosed approach can use pre-processed gelatin microgel particles as a rheology modifier for producing bulk gelatin constructs. In some embodiments, the yield stress behavior imparted by gelatin microgels may be similar to that imparted by gellan microgels. In some embodiments, however, the final composite material may have some differences. Because the gelatin particle cross-linking process is terminated by heat inactivation rather than by allowing all active sites to be consumed, the gelatin microgels may participate in covalent cross-links with the surrounding matrix as well as develop additional internal cross-links. As a result, the interphase can be exceptionally strong since it consists of both covalent bonds and non-covalent intermolecular interactions. Because both gelatin-gelatin continuous phase and filler are comprised of gelatin, which is chemically similar to native ECM and susceptible to the proteases and other factors which cells secrete to remodel their surroundings, the entire composite volume may support cell adhesion, cell-mediated local degradation, and cell migration.

In some embodiments, the combination of gelatin with microgels enables mechanically stable constructs with very low total polymer concentrations (e.g., between about 3.5% w/v and about 13% w/v), which may be beneficial since the polymer chains inhibit diffusion through the hydrogel overall. In some embodiments, a high polymer concentration makes it more difficult to supply nutrients and remove waste from cells throughout the bulk construct. Since gellan can often form robust hydrogels at extremely low concentrations compared to other biopolymers, gellan is therefore, at least according to some embodiments, well suitable as a microgel component of the composite matrix material for bulk tissue engineering applications. According to some embodiments, gelatin microgels may be better suited than gellan and/or other similar materials for applications requiring a matrix completely susceptible to cell-mediated degradation.

In some embodiments, cross-linking of the composite matrix bath material can be initiated by the addition of an enzyme, such as TG, at some point before the printing process commences, such as immediately before the printing process commences. According to some embodiments, after gently mixing the composite matrix bath material-enzyme solution to ensure homogeneous enzymatic gelation, the sacrificial material can be printed, patterned, injected, embedded, extruded, or otherwise disposed within the matrix bath material, e.g., using a 3D extrusion printing system. In some embodiments, one approach for maximizing working time and exploring fabrication of soft materials is to use the minimum gelatin concentration necessary to form a stable gel with TG. According to some of the embodiments and examples provided herein, a nominal concentration for gelatin in the matrix bath material can be about 3% w/v (though the effective concentration may be higher since pre-gelled microgels may exclude gelatin from some fraction of the total volume of the composite). In some embodiments, the enzyme (e.g., TG) concentration can be controlled in order to control gelation time, primarily, although it may also affect the final mechanical properties of the composite since the addition of serum-containing culture media often inactivates TG. According to some embodiments and examples provided herein, a concentration of about 0.5% w/v TG was found to produce stable, soft gelatin-gellan composite gels in a reasonable amount of time (within about 75 min) at a temperature of about 37° C. while allowing a reasonable printing window using an approximately 37° C. heated stage (within about 35 min).

In some embodiments, lowering TG concentration (e.g., to about 0.25% w/v) can extend the printing window to over about 1 hour, but may require an additional 2 hours to form a stable gel; this extended processing time is not ideal for cell laden structures. On the other hand, according to some embodiments, an enzyme concentration of about 1% w/v TG may shorten the printing window significantly, making it difficult to complete the printing process before gel formation causes the performance to deteriorate. By way of example only, for a composite matrix bath material comprising about 5% w/v gelatin, e.g., for gelating-5% w/v gelatin microgel composites, an enzyme concentration of about 0.5% w/v TG resulted in much faster cross-linking and a short printing window (within about 10 min), while decreasing the enzyme concentration to about 0.25% w/v TG only extended the printing window to about 20 min. This faster gelation may be attributed to the availability of cross-linking sites in both the microgel filler and the continuous matrix, which may result in faster development of a covalent network through the whole volume. By way of example only, an enzyme concentration of about 0.1% w/v TG resulted in an adequate printing window with suitable gelation speed using a gelatin concentration of about 5% w/v gelatin microgels. At a concentration of about 10% w/v gelatin microgels, the printing window for a given overall TG concentration was slightly longer, which may be due to the higher TG concentration in the microgel formation process, which may leave fewer cross-linking sites available within the microgels. As an alternative to the process described herein, a TG-free matrix with TG-supplemented ink was also contemplated and tested experimentally. Such a strategy is appealing since it likely limits matrix curing to the patterned region and/or a portion of the composite matrix bath material directly adjacent to the patterned region and because such a strategy can extend the printing window (though sometimes at the expense of consistent gel formation through the entire reservoir). However, in some of the experiments, little or no gel formation was observed.

In some embodiments, the sacrificial material is also known herein as the "ink," "sacrificial ink," and "build material." In some embodiments, one of the important characteristics or properties to consider when evaluating different materials and compositions for sacrificial material is whether the sacrificial material has suitable rheology for well-controlled printing by extrusion and whether the sacrificial material is easy to remove from the composite matrix bed material after printing. In some embodiments, an aqueous solution comprising about 2% w/v alginate in a physiological buffer (phosphate buffered saline (PBS)) can be used in the sacrificial material because it is non-toxic and readily available. In some embodiments, a non-cytotoxic porogen material can be used in the sacrificial material. It is noted that long term exposure to sodium citrate, which is typically used to liquefy cross-linked alginate templates, may cause damage to encapsulated cells. For this reason, uncross-linked alginate may also be used to make sacrificial templates for biomedical applications. However, the gelatin-gellan matrix bath formulation may instead be supplemented with calcium chloride to induce gelation of the printed sacrificial material comprising alginate, and may result in better channel morphology, which can aid perfusion through the resulting tissue construct.

For the various experimental and pilot studies conducted, the yield stress behavior of uncross-linked matrix bath formulations was quantified at 37° C., including for gelatin-gellan formulations with and without the addition of $CaCl_2$ and gelatin-gelatin formulations as shown in FIG. 4, Sections (e) and (k). Steady shear strain rate sweep data may be fit to the Herschel-Bulkley model of yield stress fluid behavior, $\sigma = \sigma_0 + K\dot{\gamma}^n$, where $\sigma$ is the total stress, $\sigma_0$ is the yield stress, $\dot{\gamma}$ is the shear rate, and K and n are fitting parameters. For gelatin-gellan composite matrix materials, the addition of $CaCl_2$ can result in a notable increase in the yield stress, e.g., according to one example an increase was observed from 0.265 Pa without the $CaCl_2$ to 1.78 Pa with $CaCl_2$ added. According to some embodiments, the low yield stress can result in very rapid and complete recovery of the composite matrix material behind the traveling tip so that printed sacrificial material can be trapped effectively within the re-jammed composite matrix material. Without wishing to be bound by any particular theory, the addition of calcium may stiffen the gellan gel particles and therefore causes an increase in the yield stress since additional force is required to deform or compress the microgels to initiate flow. For at least the same reason, the yield stress of an approximately 5% w/v gelatin concentration composite matrix bath material, e.g., for a gelatin-5% w/v gelatin composite matrix, was notably lower than the yield stress of an approximately 10% w/v gelatin concentration composite matrix bath material, e.g., a gelatin-10% w/v gelatin matrix bath material, since the 10% w/v gelatin microgels are stiffer than the 5% w/v gelatin microgels. All of the formulations tested exhibited strong shear thinning behavior after transitioning from solid-like to fluid-like behavior under shear, as shown in FIG. 4, Sections (f) and (l).

To illustrate the effect of microgels on the mechanical properties of the matrix material after curing, tensile mechanical tests were carried out on gelatin-gellan composite hydrogel specimens. Although the primary purpose of the microgel component was to adjust the rheology of the precursor, it also had a marked effect on the properties of the cured hydrogel. Representative load/displacement curves for the two materials are shown in FIG. 4, Section (f). The effective stiffness of the filled and unfilled enzymatically cross-linked gelatin was significantly different. Although the stress-strain behavior in both cases was nonlinear, reasonable agreement between replicate samples of each type was observed. The effective stiffness of the gellan composite was 14.9±2.8 kPa based on a linear approximation of the data collected after a 0.4 g preload is applied. The unfilled material was extraordinarily soft mechanically. For instance, extending specimens to approximately 300% strain (6 mm gage, 20 mm extension) exerted a barely measurable load on the test equipment so the apparent stiffness was determined to be less than 1 kPa. However, though soft, the unfilled matrix was quite elastic/resilient and mechanical behavior essentially similar over three stretching cycles.

The enhanced mechanical properties of the composite may relate to the stiffening effect that adding stiff particles to a soft matrix can have for the finished composite. In addition, because of the preparation process, preformed microgels likely excluded gelatin. This would likely confine the gelatin to the free solvent volume between microgels and likely result in a much higher effective gelatin concentration between microgel particles, which may also increase the mechanical stiffness of the composite. At least these two factors likely combine to result in a highly mechanically resilient, though still quite soft, hydrogel composite which can be intricately structured for functional objects. It should be noted that while the fabricated gelatin composite structures are quite soft, they are not particularly fragile so they can be handled and manipulated easily. Many tissues for which constructs are being formed are also quite soft, such as liver, brain, adipose, and other tissues, which have effective moduli in the same range as measured for the printed constructs described herein. Since encapsulated cells tend to respond to the stiffness of their surroundings, engineering composites that have a suitable stiffness can be an important characteristic for directing tissue development in engineered constructs.

Once the composite matrix material has been prepared and disposed within a suitable container such that the embedded printing bath is provided, the sacrificial material can be printed into the composite matrix bath. At rest, the microgel particles are usually jammed, which can cause the entire matrix bath material to behave as a solid. As the printing nozzle travels through the matrix bath during printing, the contact between the nozzle and a local portion of the composite matrix bath causes local liquefaction of the composite matrix bath material by forcing the microgels to deform and slide past one another in the surrounding gelatin solution. Thus, the liquefied composite matrix bath material flows around the nozzle and the deposited ink or sacrificial material, allowing the nozzle to move freely within the reservoir volume and permitting the sacrificial material to displace the fluidized matrix bath material. As the nozzle moves away from a region, the microgel particles revert to a jammed condition and exhibit again a solid-like behavior, trapping the deposited ink in the designed configuration. After the printing process is complete, the continuous gelatin solution present between microgels is converted to a chemically cross-linked hydrogel by the enzymatic action of, for instance, TG. Finally, the sacrificial ink is liquefied and flushed, if cross-linked during printing, or the sacrificial ink is directly flushed, if uncross-linked, from the cross-linked composite hydrogel matrix, leaving voids in the bulk hydrogel construct suitable for perfusion. In some embodiments, the method can be expanded to include sculpting of external contours by discarding excess composite hydrogel matrix after printing and cross-linking. For such bulk objects defined by solid object sculpting, manual removal of excess cross-linked matrix to release the internal sculpted object is typically required instead of fluid flushing.

Exemplary Printed Structure(s)

Referring now to FIG. 5, printed structures, including but not limited to twisted, branching, and interconnected channels, may be formed by depositing sacrificial material in gelatin-gellan or gelatin-gelatin matrix baths, respectively. While, a gelatin-gellan material is used for most examples described herein, representative patterns in an approximately 10% w/v gelatin composite hydrogel matrix, e.g., a gelatin-10% w/v gelatin composite hydrogel matrix, have also been found to exhibit comparable printing performance to other matrix bath formulations and thus may also be used, in the alternative or otherwise.

For instance, FIG. 5, Section (a) illustrates twisted channels that were designed to demonstrate the potential for truly 3D fluidic channels spanning multiple planes, which are difficult to achieve with other fabrication techniques and which enable more compact and efficient fluid handling as well as expanding the applications of microfluidic devices. This exemplary design also shows other capabilities of the embedded printing process. For example, the embedded printing process described herein facilitates the formation of planar segments in a designed configuration, the use of nonplanar segments to form continuous lumens with planar segments, the later connection of multiple segments printed at different stages in the fabrication process, and the adjustment of feature size dynamically during printing.

In some embodiments, the elasticity of the matrix bath material can make the results sensitive to the print path design. For example, in some examples, corners and junctions tended to be distorted when printed at high speeds or when print paths cross in exactly the same plane. During printing, a small volume of support material surrounding the traveling nozzle was liquefied, so sharp corners would be rounded if the nozzle was traveling too fast for the first segment to be trapped before the travel direction changed to deposit the second segment. Similarly, for in-plane path crossings, the liquefied region around the traveling nozzle, for some of the examples and experiments conducted, unjammed the matrix bath material around the previously deposited filament and distorted it as the traveling nozzle traveled across. This problem is mitigated by offsetting path crossings slightly in the z direction such that the bottom filament is largely intact but still fuses with the top filament. Intersections between channels printed during different period of the fabrication process, whether the segments form a fluidic junction or simply a continuous channel, should be designed with care as the moving nozzle disrupts a small volume of support material ahead of it so may prevent fusion of channels where the designed deposition paths only intersect at a single point.

Instead, according to some embodiments and configurations, the print path can be designed, dimensioned, configured, or caused to travel in such a way that the printing tip travels through the first filament as it deposits the second without causing the aforementioned disruption. In some examples of a twisted channel feature, segments printed at different times in the fabrication process extended nominally 0.5 mm beyond the intersection point which resulted in excellent connectivity between segments and free flow of solutions and suspensions through the connected channels. In some embodiments, larger diameter wells for infusing solutions into the channels can be formed by depositing small circular layers of sacrificial material rather than a simple post. This was found to be an effective approach, at least in some embodiments, for creating larger void volumes of specific shapes and sizes.

FIG. 5, Section (b) illustrates the feasibility of branching channels with good connectivity formed by diverging print paths. In addition, planar structures suitable for microscopic examination were of interest for in situ observation of cells within printed constructs as well as fluid dynamics. The exemplary structure illustrated in FIG. 5, Section (c) adds a layer of complexity by combining multiple branches and two discrete perfusable channel systems within the same reservoir. By way of comparison, the lattice network in the features illustrated in FIG. 5, Section (d) is a simplified version of branching channels which can be an important feature of the vasculature to model as a tissue construct. In some embodiments, such orthogonal branching networks or lattices can be used to approximate vasculature in engineered constructs since they tend to be easier to design and model than exact copies of the vascular networks which exist in vivo. More biomimetic hierarchical channel networks are also feasible, as illustrated in FIG. 5, Section (e).

In general, printing performance was found to be substantially similar for gelatin-gelatin and gelatin-gellan matrix bath formulations. Additional representative gelatin-gelatin composite constructs with printed features are shown in FIG. 5, Sections (f) and (g).

Embedded printing also enables the production of solid objects as illustrated in FIG. 6, by tracing the outer contour within a larger matrix bath reservoir (See, e.g., FIG. 6, Sections (a-b)), then curing the matrix bath material (See, e.g., FIG. 6, Section (c)) and separating the region defined by the sacrificial ink from the excess material (See, e.g., FIG. 6, Section (d)). The illustrated exemplary sculpting process is a convenient method to generate freeform soft solid hydrogel structures from structural models and medical imagery. Dumbbell-shaped structures were fabricated to demonstrate that overhanging features and well-defined edges and corners are feasible. Such structures were formed by depositing a base layer to define the bottom surface, then depositing the walls and top surface layer by layer. The internal sculpted object cures concurrently with the external hydrogel composite matrix but is entirely isolated from it by the deposited sacrificial material. After curing, the excess material can be cut or fractured to free the internal sculpted object, which can be rinsed to remove the fluidic sacrificial material from the surface. To facilitate recovery of these embedded objects, a slit may be formed by adding a line of sacrificial material in each layer to create a wall extending into the excess bulk matrix bath region from the printed contour, as shown in FIG. 6, Sections (a)-(c). After curing, this wall can form a slit in the composite hydrogel matrix which facilitates removal of excess material from the printed object (See, e.g., FIG. 6, Section (d)).

Although some matrix material is often wasted in this solid object sculpting fabrication process, it enables rapid translation of arbitrary 3D shapes from computer models to solid hydrogel objects independent of orientation and without requiring the generation of support material or infill. For example, during an experimental example presented herein, a 3D brain model was converted to G-code and printed within an hour, then cured and separated from the excess material to obtain an intact model replicating the intricate surface of the 3D model, as shown in FIG. 6, Section (e). This makes it more accessible for non-expert users of 3D printing technology, especially since typical hydrogel printing processes require extensive support bath materials or concurrent printing of mechanical reinforcements. Furthermore, the fabricated solid objects can be mostly or fully homogeneous solids meaning there may be little or no entrapped air bubbles between filaments, little or no layer interfaces, and little or no differences between perimeter and infill regions. According to some embodiments, for instance when the fabricated solid object is isotropic, swelling or shrinkage due to post-processing conditions will also be isotropic and will not likely cause structural failure or delamination.

It should be pointed out that solid object sculpting is a special application of embedded printing where embedded features can be combined to form biomedical constructs with both internal and external features. Block constructs with both external and internal features were designed and printed according to various embodiments, as shown in FIG. 6, Section (f). According to one exemplary embodiment, the blocks are formed by first printing the base, then depositing the walls and internal lattice concurrently, followed by vertical posts to connect features in different x,y planes, and finally printing the top surface. According to some embodiments, the designed blocks had smooth outer walls along with periodic orthogonal channels forming an internal network. Cell-laden printed blocks are also feasible and the printed perfusable internal features have a notable influence on their biological activity as discussed herein.

Example composite matrix bath formulations were further evaluated for biocompatibility. Living cells embedded in the composite hydrogel matrix formulations were observed to spread and proliferate over time. To compare the biocompatibility and bioactivity of at least some of the various composite hydrogel matrix formulations tested, cast cell-laden discs were cultured and cell morphology was observed on Day 1, Day 3, and Day 7 using fluorescein diacetate stain, as shown in FIG. 7, at Section (a). Unexpectedly and surprising, although the cells in the gelatin-gellan composite lagged in terms of cell extension and appeared round on day 1, the cell population in the gellan composite appeared much more active and extended than the cell population in the gelatin-gelatin composite at Days 3 and 7. As was observed, gellan microgel composites provide a hospitable environment for 3D cell culture. The lower cell activity in the gelatin-10% w/v gelatin matrix is attributed to the overall high polymer concentration of about 13%, which reduces diffusion and therefore restricts cell nutrition and exposes them to elevated levels of metabolic waste products. The lower overall polymer concentration in the gelatin-gellan composite, which was approximately 3.5%, allows more effective diffusion and supports more extensive cell activity. Furthermore, patterning of heterogeneous cell populations can be achieved in a hydrogel composite construct using the proposed embedded printing approach as seen from FIG. 7, Sections (b-d).

To demonstrate the feasibility in perfusable thick tissue fabrication using the proposed composite matrix bath formulations, cellular block constructs with embedded lattice channels, as shown schematically in FIG. 6, Section (f) and in the photographs in FIG. 8, Section (a), were printed and cultured statically for 4 days. Their metabolic activity and cell morphology were further compared with those of solid block constructs of the same composition (but lacking a printed lattice). The AlamarBlue assay results presented in FIG. 8, Section (b) show that the metabolic activity in printed constructs increased more rapidly than in solid blocks, which may indicate that the printed features improve cell activity. Cross sections from the interior of the block were also stained to observe green fluorescence from living cells and evaluate whether printed channel features improve cell survival within bulk cellular constructs. Although live cells are present in both printed and cast hydrogel constructs, they were more abundant in hollow printed structures, with extensive spreading as well as developing clusters of cells due to proliferation. Representative images of central cross sections (showing regions away from the edges of the blocks) are shown in FIG. 8, Sections (c) and (d). In particular, a perfusion channel is visible in FIG. 8, Section (c).

In terms of the quality of printing, two of the major factors which affect the outcome of a printing process are the composite material selection and the printing parameters. For instance, there were found to be effects on finished, printed article based on the properties and characteristics of the composite matrix material(s) chosen. For example, the rheological properties of the matrix bath were observed to shift during the printing process as the enzyme (e.g., TG) was added and as the enzyme begins to catalyze cross-linking within the matrix bath, transforming the yield stress precursor to a covalently cross-linked composite hydrogel matrix. As a result, the printing performance was also affected. This change in printing quality was assessed by printing a number of channels at timed intervals after the addition of the enzyme to the matrix bath, then curing and sectioning the gel block to observe the channel morphology.

A gradual shift from perfectly round (e.g., from an aspect ratio of 1.066 and a roundness of 0.938) to significantly elongated (e.g., to an aspect ratio of 2.057 and a roundness of 0.486) channels was observed from immediately after mixing the enzyme into the composite matrix bath (e.g., a gelatin-gellan matrix bath) until about 40 minutes after mixing, as illustrated in FIG. 9. After this duration, attempting to print in the partially cured matrix bath caused tearing as the matrix material deformed elastically and eventually fractured rather than flowing around the traveling nozzle. Deposited sacrificial material did not form well-defined features under these conditions, as indicated by the large error bars at late time points in FIG. 9. Allowing approximately 5 minutes for loading the enzyme-supplemented matrix material in the reservoir and assuming a speed of about 150 mm/min, it was determined to be possible to print greater than about 5 meters of sacrificial material before the performance deteriorates significantly (e.g., a 35 min duration×a 150 mm/min print speed=5,250 mm print length=5.25 meters print length). This translates, for example, to a 1×2×2 cm construct with no cell further than 200 µm from a 600 µm diameter printed channel.

With regard to the effects of fabrication parameters on printing quality, the channel size and morphology for thick perfusable tissue constructs varied depending on the tip size, printing parameters, and printing time. The minimum achievable channel size was primarily controlled by tip or nozzle dimensions and form factor in this displacement-based printer where the flow rate was automatically adjusted to match the travel speed. However, larger circular channels can be easily produced by traversing the same print path multiple times. Attempts to print small channels using a low flow rate through a relatively large tip or nozzle tended to result in poorly-shaped (but intact) channels for which the cross section was triangular due to the wide void space created behind the tip. In general, the shape of the channel cross section deteriorated over the course of the printing process as the matrix material's recovery behind the tip becomes slower and less complete. This was visible during printing as an increasing tendency of the matrix bath around the tip to deform elastically rather than simply flow around it. After printing, the most noticeable effect of longer printing time was transition to vertically elongated or tear-drop shaped channel cross sections, in contrast to the ideal circular cross section of features printed immediately after matrix preparation. As used herein, the 'printing window' is defined as the longest time after matrix preparation when reasonably circular cross sections are observed. For some or more of the embodiments and examples discussed herein, the printing window was found to be about 35 min. The minimum gap between channels is similar in both the x,y plane and for vertical z stacking, and is approximately equal to the filament width.

Referring now to FIG. 10, an exemplary method 30 is described for embedded printing of a perfusable tissue construct. In some embodiments, cells can be harvested from a patient for use in printing the tissue construct, at 31. In some embodiments, the cells used for this application could be harvested from a patient and incorporated into a printed tissue construct as needed for clinical treatments. Inn some embodiments, a matrix bath material can be formed from microgels, an uncross-linked polymer material, and the cells harvested from the patient, while the sacrificial ink is formed from a polymer solution, at 32. The matrix bath material is disposed into the bath container and the sacrificial ink is then printed into the matrix bath material using a nozzle that travels a predetermined route through the matrix bath material during printing of the sacrificial structure from the sacrificial ink, at 33. The matrix bath material is then cross-linked, such as by adding an enzyme that causes enzymatic cross-linking, at 34. Enzymatic cross-linking can be terminated by heating the bed to above a threshold temperature sufficient to cease enzymatic activities. Once cross-linking is complete, the resulting tissue construct can be perfused to remove the sacrificial ink, leaving behind one or more voids, such as conduits, lumens, vessels, or the like, at 35. The resulting vascularized thick tissue construct is then removed and cleaned, at 36. The vascularized thick tissue construct can then be tested to ensure proper vascularity, proper perfusion rate, to detect any flaws in the printed construct, and the like. Once the vascularized thick tissue construct is confirmed to be properly formed, it is ready for implantation to the patient, at 37. In some embodiments, since the initial cells that were harvested from the patient and included in the matrix bath material were harvested from the same individual as the patient to whom the tissue construct is being implanted, there may be a reduced risk of rejection of the implanted tissue construct based upon an immune system reaction or the like.

Described herein are methods, apparatuses, and systems, according to some embodiments, for the use of a microgel-filled cross-linkable yield stress composite hydrogel as a matrix bath to enable embedded patterning of sacrificial materials to generate engineered tissue constructs with perfusable internal channels. The combination of yield-stress fluid behavior from the microgel filler (such as gellan and gelatin) and susceptibility to covalent cross-linking from the continuous phase (such as the gelatin and TG mixture) was identified as enabling rapid custom fabrication of mechanically robust perfusable engineered constructs laden with cells. This approach has potential for both in vitro and in vivo applications and may be especially useful for chip-based systems where traditional printing methods would have difficulty depositing a cell-laden matrix to completely fill a pre-existing cavity.

Both 2D and 3D fluidic networks were demonstrated using the composite matrix bath. Networked channels were found to increase the metabolic activity of living cells in the cross-linked matrix. In addition, the yield stress microgel composite matrix bath also enables solid object sculpting by printing a sacrificial material to define the object external contour in a composite matrix bath as well as patterning of heterogeneous cell populations within a bulk construct. This solid object sculpting method may be particularly useful for generating patient-specific models with properties analogous to native tissue to aid in medical training and facilitate surgical planning. For example, customized, implantable printed constructs may also be readily fabricated based on medical imaging of specific tissue defects.

Specific Examples

The gelatin-gellan matrix bath material was prepared by dissolving 3% w/v gelatin and 6.8 mM $CaCl_2$ (0.1% w/v $CaCl_2.2H_2O$) as needed in jammed 0.5% w/v gellan microgels, then adding transglutaminase. Gellan microgel dispersions were prepared by dispersing the appropriate mass of low acyl gellan (Kelcogel F low acyl gellan gum, Modernist Pantry, York, Me.) in phosphate buffered saline (PBS, Corning cellgro, Manassas, Va.) in conical vials, then placing the closed vials in a boiling water bath for at least 20 minutes for full dissolution. After cooling completely, the bulk hydrogel was pressed through a stainless steel mesh (140 mesh, 100 µm holes) for consistent fragmentation into a jammed microgel dispersion. Then, the appropriate mass of gelatin (225 bloom, type A, from porcine skin, MP Biomedicals, Solon, Ohio) and calcium chloride (calcium chloride dihydrate, Sigma-Aldrich, St. Louis, Mo.) as needed was added to the jammed microgels and allowed to dissolve at 37° C. until a clear mixture was obtained. To enable rapid and efficient addition of TG to the matrix mixture, a 20 wt % stock solution of tranglutaminase (MooGloo TI, Modernist Pantry, York, Me.) was prepared by dissolving the dry powder in PBS; the mixture was vortexed briefly and maintained at 37° C. for 20 minutes to dissolve the enzyme (TG), then stored at 4° C. until use. Immediately before printing, TG stock was added to the warm matrix mixture for a final concentration of 0.5 wt %. The warm mixture was gently mixed and centrifuged to remove bubbles before loading in the print bath for patterning. Immediately after loading the matrix material (0.5% gellan, 3% gelatin, 0.5% TG, and 6.8 mM $CaCl_2$ as needed) in the print reservoir, the reservoir was placed on the heated print bed and the sacrificial ink was deposited to create features within the material. After the printing process was complete, the print reservoir was held at 37° C. for 75 minutes for full cross-linking.

Gelatin microgels were prepared by fragmenting a bulk covalently cross-linked gel. Gelatin was dissolved in PBS at 37° C. to make a 22.2% w/v solution. A 20% w/v stock solution of TG (Moo Gloo TI, Modernist Pantry, York Me.) in PBS was prepared separately by dispersing the powder in PBS, vortexing briefly, then incubating at 37 C for 20 minutes; TG stock was stored at 4 C for up to one week before use. The two solutions were mixed at a 9:1 ratio for final concentrations of 20% w/v gelatin and 2% w/v TG, and incubated for 4 hr at 37 C for gel formation in a conical vial. 5% and 10% w/v gelatin gels were prepared analogously, keeping the 10:1 ratio between gelatin and TG constant (that is, they were cross-linked using 0.5% and 1.0% w/v TG, respectively). The vial of covalently cross-linked gel was then placed in boiling water for 20 min to deactivate TG. Finally, the bulk gel was placed in a beaker with deionized water for a total volume of ~200 mL and fragmented using a household immersion blender on high for 5 min. Excess water was removed by centrifuging the microgel mixture (5 min at 4200 rpm) and discarding the watery supernatant; the packed microgels were then stored at 4° C. until use.

In addition, the covalently cross-linked gelatin microgels were also autoclaved at 121° C. for 60 min to prepare materials for cell culture; excess PBS was added prior to autoclaving to prevent desiccation of the microgels, and they were re-collected by centrifuging after sterilization.

Gelatin composites were prepared by combining dry gelatin with gelatin microgels. Typically, 0.3 g gelatin was combined with 10.0 g gelatin microgels to make a composite curable matrix precursor. As needed, 6.8 mM $CaCl_2$ (0.1% w/v $CaCl_2 \cdot 2H_2O$) was added for alginate gelation. The mixture was warmed to 37° C. and mixed thoroughly until homogeneous, then combined with TG stock immediately before printing.

The alginate-based sacrificial ink was prepared by dissolving 2% w/v alginate (alginic acid, sodium salt, Acros Organics, Waltham Mass.) in PBS.

NIH 3T3 fibroblasts were harvested, pelleted, and resuspended for this work. For biocompatibility assessment and cell patterning studies, cells were resuspended in the warm gelatin-gelatin matrix bath mixture before adding TG stock solution. For morphology evaluation, the cell-laden matrix was cast in a 24-well plate. For cell patterning, the cell-laden matrix was loaded in a sterilized syringe for dispensing into a cast acellular matrix bath.

For printed cell-laden structures, cells were resuspended in the warm gelatin-gellan matrix bath mixture with calcium at $2.5 \times 10^6$ cells/mL just before adding the TG stock solution. Cellular structures were printed with a 30 gauge tip. To verify that cells remained viable and that the matrix supported adhesion and cellular interactions, cast discs of the cell laden matrix material without printed features were initially fabricated and cultured for several days. Cell-laden structures were incubated in complete culture media (Dulbecco's modified Eagle's medium (DMEM, Sigma-Aldrich, St. Louis, Mo.) with 10% Fetal Bovine Serum (FBS) (HyClone, Logan, Utah)) in a humidified 5% $CO_2$ incubator. Metabolic activity was assessed on 1, 2, 3, and 4 using the alamarBlue assay (ThermoFisher Scientific, Waltham, Mass.) according to the manufacturer's instructions except that the incubation time was extended to 6 hours; fluorescent intensity was recorded using a plate reader (Synergy HT, Biotek, Winooski, Vt.). Data was further processed using Microsoft Excel. Cellular constructs were stained with fluorescein diacetate (FDA) by immersing specimens in PBS containing 8 µg/mL FDA. Transmitted light and fluorescent images were captured using a digital fluorescent microscope (EVOS, XL Core, Thermo Fisher Scientific, Waltham, Mass.).

Rheological properties were measured using a rheometer (MCR-702 TwinDrive, Anton-Paar, Graz, Austria) with a 25 mm sandblasted (Ra=4.75 m) parallel-plate measuring geometry, 1 mm gap. Samples were subjected to a preshear step (100 s−1 for 30 sec) followed by a 60 sec recovery period to eliminate loading effects. To determine the yield stress quantitatively, steady rate sweeps were conducted by varying the shear rate from 100 s−1 to 0.01 s−1, and the stresses were measured at different shear rates. The effect of the gellan microgel filler on the mechanical properties of the covalent gelatin gel were evaluated using tensile mechanical tests. Dogbone shaped samples of either the print matrix, prepared as described herein, or gellan-free 3% w/v gelatin in PBS with 0.5% w/v TG, were cast in PDMS molds. The molds were prepared from machined aluminum masters and had nominal gage dimensions of 0.5 mm thick×1.25 mm wide×6 mm long; the hydrogel precursors were allowed to cure at 37° C. for 60 minutes, then carefully demolded and immediately tested. Specimens were clamped in a micromechanical testing apparatus (eXpert 4000 MicroTester, Admet, Norwood, Mass.) and stretched at 5 mm/min to a maximum extension of 10 mm or 20 mm. Each sample was subjected to three stretching cycles in rapid succession. Data was exported to Microsoft Excel for further processing.

For printing, a Hyrel Engine SR 3D (Hyrel3D, Norcross, Ga.) printer with a CSD-5 head (UV array removed for these experiments) was utilized with various gauge stainless steel tips (Norsdon EFD, Vilters, Switzerland). Custom G-code scripts for simple structures were generated manually; more complex structures were designed using SolidWorks, exported as STL files, and sliced using the embedded Slic3r tools in the Repetrel control software for the Hyrel3D printer. Although exact settings varied slightly, the layer height setting was typically ~0.5× the nozzle width, and the print speed was set at 2.5-5 mm/sec in the x and y directions and 2.5 mm/sec in the z direction.

After printing, constructs with embedded sacrificial ink were allowed to cross-link at 37° C. for 45 min. Then, the sacrificial ink was removed from channels or the sculpted objects were separated manually from excess matrix material. In cases where the sacrificial material did not form a gel (alginate in calcium-free matrix formulations), the fluid sacrificial material was simply flushed from internal channels by infusing water (acellular constructs) or PBS (cell-laden constructs). For alginate sacrificial ink in calcium-containing matrix formulations, soaking in 1.62% w/v sodium citrate (molecular biology grade, BDH, USA) for several hours was necessary to fully liquefy the sacrificial ink within perfusable features so that they could be flushed with other fluids. Sculpted objects were recovered by simply manually separating the internal sculpted object from excess matrix material; soaking in citrate facilitated this process when alginate sacrificial ink was used with calcium-containing matrix formulations, but was not essential.

According to at least some embodiments, apparatuses, systems, and methods are provided for fabricating engineered tissue constructs. For example, according to some embodiments, a method, along with the associated system and apparatus, are provided for additive manufacturing of tissue constructs by printing a build material into a support bath.

According to some embodiments described herein, a method is provided for embedded printing of perfusable tissue constructs, the method comprising: providing a composite matrix bath comprising a microgel filler and a hydrogel precursor; disposing, using an extrusion tip configured to travel along a predefined course through the composite matrix bath, a volume of a sacrificial material into the composite matrix bath, wherein the volume of sacrificial material disposed along the predefined course is retained within the composite matrix bath; allowing the volume of the sacrificial material to at least partially solidify; and removing the volume of the at least partially solidified sacrificial material from the composite matrix bath to form one or more voids substantially similar in volume and form factor to the volume of the at least partially solidified sacrificial material.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, a method such as that described above may further comprise cross-linking the hydrogel precursor to change one or more rheological properties of the composite matrix bath. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change, e.g., using transglutaminase.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

According to other embodiments described herein, a system is provided for embedded printing of perfusable tissue constructs, the system comprising: a composite matrix bath comprising a microgel filler and a hydrogel precursor; a reservoir configured to store a supply of a sacrificial material; and an extrusion tip configured to travel along a predefined course through the composite matrix bath and dispose at various points along the predefined course the sacrificial material into the composite matrix bath. In some embodiments, the volume of sacrificial material disposed along the predefined course is retained within the composite matrix bath. In some embodiments, the volume of the sacrificial material, once disposed within the composite matrix bath, at least partially solidifies. In some embodiments, once the volume of the at least partially solidified sacrificial material is removed from the composite matrix bath, one or more voids are formed that are substantially similar in volume and form factor to the volume of the at least partially solidified sacrificial material.

In some embodiments, the one or more voids formed once the at least partially solidified sacrificial material is removed from the composite matrix bath comprise a network of microfluidic channels operable to perfuse a fluid therethrough. In some embodiments, the composite matrix bath comprises one or more acellular or cell-laden hydrogels. In some embodiments, the sacrificial material comprises a salt and a physiological buffer or a non-cytotoxic porogen material.

In some embodiments, the hydrogel precursor is operable to be cross-linked to change one or more rheological properties of the composite matrix bath. In some embodiments, the hydrogel precursor comprises at least one of gellan-containing microgels, gelatin-containing microgels, or other hydrogel-based biocompatible microgels. In some embodiments, said cross-linking comprises cross-linking the hydrogel precursor using chemical agents, enzymatic agents, physical cross-linking methods, or a temperature change, e.g., using transglutaminase.

In some embodiments, the composite matrix bath is substantially solid-like at rest, and wherein, as the extrusion tip travels along the predefined course, a portion of the composite matrix bath adjacent to the traveling extrusion tip is liquified, allowing the sacrificial material to be disposed along the predefined course, and as the extrusion tip continues along the predefined course, the portion of the composite matrix bath adjacent the disposed sacrificial material reverts to being substantially solid-like.

According to yet other embodiments described herein, a method is provided for embedded printing, the method comprising: preparing a composite matrix bath comprising a microgel filler and a hydrogel precursor; disposing, using an extrusion tip configured to travel along a predefined course through the composite matrix bath, a volume of a sacrificial material into the composite matrix bath, wherein the volume of sacrificial material disposed along the predefined course is retained within the composite matrix bath; allowing the volume of the sacrificial material to at least partially solidify; cross-linking, e.g., enzymatically cross-linking, the hydrogel precursor to change one or more rheological properties of the composite matrix bath; and terminating cross-linking by heating the composite matrix bath to a temperature greater than a temperature threshold.

In some embodiments, the sacrificial material comprises a salt and a physiological buffer or a non-cytotoxic porogen material, and the hydrogel precursor comprises at least one of gellan-containing microgels, gelatin-containing microgels, or other hydrogel-based biocompatible microgels. In some embodiments, the sacrificial material comprises alginate and phosphate buffered saline, the hydrogel precursor comprises gellan-based microgels and gelatin-based microgels, and the composite matrix bath further comprises calcium chloride, the calcium chloride operable to induce gelation of the printed sacrificial material.

In some embodiments, methods such as that describe above can further comprise removing the volume of the at least partially solidified sacrificial material from the composite matrix bath to form one or more voids substantially similar in volume and form factor to the volume of the at least partially solidified sacrificial material.

In some embodiments, one or more of the operations, steps, elements, or processes described herein may be modified or further amplified as described below. Moreover, in some embodiments, additional optional operations may also be included. It should be appreciated that each of the modifications, optional additions, and/or amplifications described herein may be included with the operations previously described herein, either alone or in combination, with any others from among the features described herein.

Although specific advantages have been enumerated above, various embodiments may include some, none, or all of the enumerated advantages.

Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

The provided method description, illustrations, and process flow diagrams are provided merely as illustrative examples and are not intended to require or imply that the steps of the various embodiments must each or all be performed and/or should be performed in the order presented or described. As will be appreciated by one of skill in the art, the order of steps in some or all of the embodiments described may be performed in any order. Words such as "thereafter," "then," "next," etc. are not intended to limit the order of the steps; these words are simply used to guide the reader through the description of the methods. Further, any reference to claim elements in the singular, for example, using the articles "a," "an," or "the" is not to be construed as limiting the element to the singular. Further, any reference to dispensing, disposing, depositing, dispersing, conveying, injecting, conveying, inserting, communicating, and other such terms of art are not to be construed as limiting the element to any particular means or method or apparatus or system, and is taken to mean conveying the material within the receiving vessel, solution, conduit, or the like by way of any suitable method.

As used herein, the term "about" and "approximately" generally mean plus or minus 10% of the value stated, for example about 250 μm would include 225 μm to 275 m, approximately 1,000 μm would include 900 μm to 1,100 m.

Conventional terms in the fields of tissue engineering, materials science, and chemistry have been used herein. The terms are known in the art and are provided only as a non-limiting example for convenience purposes. Accordingly, the interpretation of the corresponding terms in the claims, unless stated otherwise, is not limited to any particular definition. Thus, the terms used in the claims should be given their broadest reasonable interpretation.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation. Specific equipment and materials described in the examples are for illustration only and not for purposes of limitation. For instance, any and all articles, portions of articles, structures, bulk materials, and/or the like, having any form factors, scale, dimensions, aesthetic attributes, material properties, internal structures, and/or mechanical properties, which are formed according to any of the disclosed methods, approaches, processes, or variations thereof, using any devices, equipment, apparatuses, systems, or variations thereof, using any of the build material, printing mixture, ink, yield-stress support material, or other material compositions described herein or variations thereof, are all contemplated and covered by the present disclosure. None of the examples provided are intended to, nor should they, limit in any way the scope of the present disclosure.

Every document cited or referenced herein or cited or referenced in the priority document, including any cross referenced or related patent or application is hereby incorporated herein by reference in its entirety unless expressly excluded or otherwise limited. The citation of any document and/or the mention of methods or apparatuses as being conventional, typical, usual, or the like is not, and should not be taken as an acknowledgement or any form of suggestion that the reference or mentioned method/apparatus is prior art with respect to any invention disclosed or claimed herein or that it alone, or in any combination with any other reference or references, teaches, suggests or discloses any such invention or forms part of the common general knowledge in any country in the world. Further, to the extent that any meaning or definition of a term in this document conflicts with any meaning or definition of the same term in a document incorporated by reference, the meaning or definition assigned to that term in this document shall govern.

The various portions of the present disclosure, such as the Background, Summary, Brief Description of the Drawings, and Abstract sections, are provided to comply with requirements of the MPEP and are not to be considered an admission of prior art or a suggestion that any portion or part of the disclosure constitutes common general knowledge in any country in the world.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The invention claimed is:

1. A system for embedded printing of perfusable tissue constructs, the system comprising:
   a composite matrix bath comprising a microgel filler comprising one or more of gellan or gelatin and a hydrogel precursor comprising gelatin;
   a reservoir configured to store a supply of a sacrificial material;
   an extrusion tip configured to travel along a predefined course through the composite matrix bath and dispose at various points along the predefined course a volume of the sacrificial material into the composite matrix bath; and
   a computing device configured to:
      cause the extrusion tip to travel along the predefined course and dispose the volume of sacrificial material within the composite matrix bath, such that the volume of the sacrificial material, once disposed within the composite matrix bath, at least partially solidifies or has limited diffusion between it and the composite matrix bath.

2. The system of claim 1, wherein one or more voids are formed once the volume of the sacrificial material is removed from the composite matrix bath, wherein the one or more voids comprise a network of microfluidic channels operable to perfuse a fluid therethrough.

3. The system of claim 1, wherein the composite matrix bath comprises one or more acellular or cell-laden hydrogels.

4. The system of claim 1, wherein the sacrificial material comprises a salt and a physiological buffer.

5. The system of claim 1, wherein the hydrogel precursor is operable to be cross-linked to change one or more rheological properties of the composite matrix bath.

6. The system of claim 5, wherein said cross-linking comprises cross-linking the hydrogel precursor using chemical agents, enzymatic agents, physical cross-linking methods, or a temperature change.

7. The system of claim 1, wherein:
   the composite matrix bath is substantially solid-like at rest,
   as the extrusion tip travels along the predefined course, a portion of the composite matrix bath adjacent to the traveling extrusion tip is liquified, allowing the sacrificial material to be disposed along the predefined course, and
   as the extrusion tip continues along the predefined course, the portion of the composite matrix bath adjacent the disposed sacrificial material reverts to being substantially solid-like.

8. A method for embedded printing of perfusable tissue constructs, the method comprising:
   providing a system comprising:
      a composite matrix bath comprising a microgel filler comprising one or more of gellan or gelatin and a hydrogel precursor comprising gelatin,
      a reservoir configured to store a supply of a sacrificial material, and
      an extrusion tip configured to travel along a predefined course through the composite matrix bath and dispose at various points along the predefined course the sacrificial material into the composite matrix bath;
   communicating, from the reservoir, to the extrusion tip, a volume of the sacrificial material;
   causing the extrusion tip to travel along a predefined course through the composite matrix bath;
   disposing, using the extrusion tip, while the extrusion tip is caused to travel along the predefined course through the composite matrix bath, the volume of the sacrificial material into the composite matrix bath, wherein the volume of sacrificial material disposed along the predefined course is retained within the composite matrix bath; and
   allowing the volume of the sacrificial material to at least partially solidify or have limited diffusion.

9. The method of claim 8, wherein one or more voids are formed once the sacrificial material is removed from the composite matrix bath, and wherein the one or more voids comprise a network of microfluidic channels operable to perfuse a fluid therethrough.

10. The method of claim 8, wherein the composite matrix bath comprises one or more acellular or cell-laden hydrogels.

11. The method of claim 8, wherein the sacrificial material comprises a salt and a physiological buffer.

12. The method of claim 8, further comprising:
   cross-linking the hydrogel precursor to change one or more rheological properties of the composite matrix bath.

13. The method of claim 12, wherein said cross-linking comprises cross-linking the hydrogel precursor using chemical agents, enzymatic agents, physical cross-linking methods, or a temperature change.

14. The method of claim 8, wherein:
   the composite matrix bath is substantially solid-like at rest,
   as the extrusion tip travels along the predefined course, a portion of the composite matrix bath adjacent to the traveling extrusion tip is liquified, allowing the sacrificial material to be disposed along the predefined course, and
   as the extrusion tip continues along the predefined course, the portion of the composite matrix bath adjacent the disposed sacrificial material reverts to being substantially solid-like.

15. An apparatus for embedded printing of perfusable tissue constructs, the apparatus comprising:
   an extrusion tip; and
   a computing device configured to cause movement of the extrusion tip along a predefined course through a composite matrix bath and cause the extrusion tip to dispose a sacrificial material into the composite matrix bath at various points along the predefined course,
   wherein the composite matrix bath comprises a microgel filler comprising one or more of gellan or gelatin and a hydrogel precursor comprising gelatin;
   wherein the sacrificial material disposed along the predefined course is retained within the composite matrix bath and at least partially solidifies or have limited diffusion,
   wherein the computing device is configured to cause cross-linking of the hydrogel precursor to change one or more rheological properties of the composite matrix bath, and
   wherein the computing device is configured to cause termination of the cross-linking by heating the composite matrix bath to a temperature greater than a temperature threshold.

16. The apparatus of claim 15, wherein
the sacrificial material comprises a salt and a physiological buffer.

17. The apparatus of claim 16, wherein:
the sacrificial material comprises alginate and phosphate buffered saline, and
the composite matrix bath further comprises calcium chloride, the calcium chloride operable to induce gelation of the printed sacrificial material.

18. The apparatus of claim 15, wherein the computing device is further configured to:
remove the sacrificial material from the composite matrix bath to form one or more voids substantially similar in volume and form factor to the volume of the sacrificial material.

* * * * *